(12) United States Patent
Guild et al.

(10) Patent No.: US 10,143,758 B2
(45) Date of Patent: Dec. 4, 2018

(54) LIVER SPECIFIC DELIVERY OF MESSENGER RNA

(71) Applicant: TRANSLATE BIO, INC., Cambridge, MA (US)

(72) Inventors: Braydon Charles Guild, Concord, MA (US); Frank DeRosa, Chelmsford, MA (US); Michael Heartlein, Boxborough, MA (US)

(73) Assignee: Translate Bio, Inc., Lexington, MA (US)

( * ) Notice: Subject to any disclaimer, the term of this patent is extended or adjusted under 35 U.S.C. 154(b) by 469 days.

(21) Appl. No.: 13/800,501

(22) Filed: Mar. 13, 2013

(65) Prior Publication Data

US 2013/0195967 A1   Aug. 1, 2013

Related U.S. Application Data

(62) Division of application No. 12/957,340, filed on Nov. 30, 2010, now abandoned.

(60) Provisional application No. 61/265,653, filed on Dec. 1, 2009.

(51) Int. Cl.
| | |
|---|---|
| *A61K 48/00* | (2006.01) |
| *A61K 9/00* | (2006.01) |
| *A61K 9/127* | (2006.01) |
| *C07J 43/00* | (2006.01) |
| *C12N 15/67* | (2006.01) |
| *A61K 31/7105* | (2006.01) |

(52) U.S. Cl.
CPC ........ *A61K 48/0033* (2013.01); *A61K 9/0019* (2013.01); *A61K 9/1271* (2013.01); *A61K 9/1272* (2013.01); *A61K 31/7105* (2013.01); *A61K 48/005* (2013.01); *A61K 48/0008* (2013.01); *C07J 43/003* (2013.01); *C12N 15/67* (2013.01)

(58) Field of Classification Search
None
See application file for complete search history.

(56) References Cited

U.S. PATENT DOCUMENTS

| | | | |
|---|---|---|---|
| 4,737,323 | A | 4/1988 | Martin et al. |
| 4,920,016 | A | 4/1990 | Allen et al. |
| 4,946,683 | A | 8/1990 | Forssen |

(Continued)

FOREIGN PATENT DOCUMENTS

| | | |
|---|---|---|
| CA | 2807552 A1 | 2/2012 |
| WO | WO-1996/37211 A1 | 11/1996 |

(Continued)

OTHER PUBLICATIONS

Cassiman, Current Pharmaceutical Design, 2011, 17: 2550-2557.*

(Continued)

*Primary Examiner* — Ileana Popa
(74) *Attorney, Agent, or Firm* — Proskauer Rose LLP; Fangli Chen

(57) ABSTRACT

Disclosed herein are compositions and methods of modulating the expression of gene or the production of a protein by transfecting target cells with nucleic acids. The compositions disclosed herein demonstrate a high transfection efficacy and are capable of ameliorating diseases associated with protein or enzyme deficiencies.

30 Claims, 4 Drawing Sheets

Specification includes a Sequence Listing.

(56) References Cited

U.S. PATENT DOCUMENTS

| | | | |
|---|---|---|---|
| 5,194,654 | A | 3/1993 | Hostetler et al. |
| 5,223,263 | A | 6/1993 | Hostetler et al. |
| 5,279,833 | A | 1/1994 | Rose |
| 5,677,124 | A | 10/1997 | DuBois et al. |
| 5,744,335 | A | 4/1998 | Wolff et al. |
| 5,844,107 | A | 12/1998 | Hanson et al. |
| 5,885,613 | A | 3/1999 | Holland et al. |
| 6,147,055 | A | 11/2000 | Hobart et al. |
| 6,165,763 | A | 12/2000 | Brown et al. |
| 6,214,804 | B1 | 4/2001 | Felgner et al. |
| 6,271,208 | B1 | 8/2001 | Bischoff |
| 6,287,951 | B1 | 9/2001 | Semple et al. |
| 6,417,326 | B1 | 7/2002 | Cullis et al. |
| 6,534,484 | B1 | 3/2003 | Wheeler et al. |
| 6,586,410 | B1 | 7/2003 | Wheeler et al. |
| 6,670,178 | B1 | 12/2003 | Selden et al. |
| 6,733,777 | B2 | 5/2004 | Erbacher et al. |
| 6,743,823 | B1 | 6/2004 | Summar et al. |
| 6,790,838 | B2 | 9/2004 | Alison et al. |
| 6,815,432 | B2 | 11/2004 | Wheeler et al. |
| 6,835,395 | B1 | 12/2004 | Semple et al. |
| 6,858,224 | B2 | 2/2005 | Wheeler et al. |
| 6,858,225 | B2 | 2/2005 | Semple et al. |
| 7,067,697 | B2 | 6/2006 | Gao |
| 7,341,738 | B2 | 3/2008 | Semple et al. |
| 8,021,686 | B2 | 9/2011 | Semple et al. |
| 8,691,966 | B2 | 4/2014 | Kariko et al. |
| 8,748,089 | B2 | 6/2014 | Kariko et al. |
| 8,835,108 | B2 | 9/2014 | Kariko et al. |
| 8,846,348 | B2 | 9/2014 | Jendrisak et al. |
| 2003/0083272 | A1 | 5/2003 | Wiederholt et al. |
| 2004/0110709 | A1 | 6/2004 | Li et al. |
| 2005/0032730 | A1 | 2/2005 | Von der Mulbe et al. |
| 2005/0054026 | A1 | 3/2005 | Atsushi et al. |
| 2005/0059624 | A1 | 3/2005 | Hoerr et al. |
| 2005/0065107 | A1 | 3/2005 | Hobart et al. |
| 2005/0250723 | A1 | 11/2005 | Hoerr et al. |
| 2006/0008910 | A1* | 1/2006 | MacLachlan et al. ........ 435/458 |
| 2006/0083780 | A1 | 4/2006 | Heyes et al. |
| 2006/0172003 | A1 | 8/2006 | Meers et al. |
| 2006/0204566 | A1 | 9/2006 | Smyth-Templeton et al. |
| 2007/0252295 | A1 | 11/2007 | Panzner et al. |
| 2007/0281336 | A1 | 12/2007 | Jendrisak et al. |
| 2008/0260706 | A1 | 10/2008 | Rabinovich et al. |
| 2009/0093433 | A1 | 4/2009 | Woolf et al. |
| 2009/0186805 | A1 | 7/2009 | Tabor et al. |
| 2009/0221684 | A1 | 9/2009 | Grinstaff et al. |
| 2010/0028943 | A1 | 2/2010 | Thomas et al. |
| 2010/0047261 | A1 | 2/2010 | Hoerr et al. |
| 2010/0189729 | A1 | 7/2010 | Hoerr et al. |
| 2010/0267806 | A1 | 10/2010 | Bumcrot et al. |
| 2011/0038941 | A1 | 2/2011 | Lee et al. |
| 2011/0244026 | A1 | 10/2011 | Guild et al. |
| 2012/0065252 | A1 | 3/2012 | Schrum et al. |
| 2012/0195936 | A1 | 8/2012 | Rudolph et al. |
| 2012/0237975 | A1 | 9/2012 | Schrum et al. |
| 2012/0251618 | A1 | 10/2012 | Schrum et al. |
| 2014/0162897 | A1 | 6/2014 | Grunenwald et al. |
| 2014/0206753 | A1 | 7/2014 | Guild et al. |
| 2014/0294938 | A1 | 10/2014 | Guild et al. |
| 2014/0294939 | A1 | 10/2014 | Guild et al. |
| 2014/0294940 | A1 | 10/2014 | Guild et al. |

FOREIGN PATENT DOCUMENTS

| | | |
|---|---|---|
| WO | WO 02/34236 | 5/2002 |
| WO | WO-02/34236 A2 | 5/2002 |
| WO | WO-2005/037226 A2 | 4/2005 |
| WO | WO 2007/024708 | 3/2007 |
| WO | WO-2007/024708 A2 | 3/2007 |
| WO | WO-2007/120863 A2 | 10/2007 |
| WO | WO-2007/126386 A1 | 11/2007 |
| WO | WO 2008/083949 | 7/2008 |
| WO | WO-2008/083949 A2 | 7/2008 |
| WO | 2009127060 † | 10/2009 |
| WO | WO 2009/127230 | 10/2009 |
| WO | WO-2009/127230 A1 | 10/2009 |
| WO | WO 2010/054401 | 5/2010 |
| WO | WO-2010/054401 A1 | 5/2010 |
| WO | WO 2010/054405 | 5/2010 |
| WO | WO-2010/054405 A1 | 5/2010 |
| WO | WO-2010/119256 A1 | 10/2010 |
| WO | WO 2010/144740 | 12/2010 |
| WO | WO-2010/144740 A1 | 12/2010 |
| WO | WO-2011/068810 A1 | 6/2011 |
| WO | WO-2012/019168 A2 | 2/2012 |
| WO | WO 2012/019630 | 2/2012 |
| WO | WO-2012/019630 A1 | 2/2012 |
| WO | WO 2012/019780 | 2/2012 |
| WO | WO-2012/019780 A1 | 2/2012 |
| WO | WO-2012/045075 A1 | 4/2012 |
| WO | WO-2012/045082 A2 | 4/2012 |
| WO | WO-2012/135805 A2 | 10/2012 |
| WO | WO-2013/039857 A1 | 3/2013 |
| WO | WO-2013/039861 A2 | 3/2013 |

OTHER PUBLICATIONS

Gonzalez Aseguinolaza et al., Clinics and Research in Hepatology and Gastroenterology, 2011, 35: 699-708.*

Anderson et al., Human Gene Therapy, 2003, 14: 191-202.*

Raper et al., J Inher Metab Dis, 1998, 21: 119-137.*

Yamamoto et al., European Journal of Pharmaceutics and Biopharmaceutics, 2009, 71: 484-489.*

Barreau et al., RNA, 2006, 12: 1790-1793.*

Ye et al., J Biol Chem, 1996, 271, 7: 3639-3646.*

Okumura et al., J Gene Med, online Jun. 19, 2008, 10: 910-917.*

Kariko et al., Mol Ther, Nov. 2008, 16: 1833-1840.*

Lu et al., Cancer Gene Therapy, 1994, 1: 245-252.*

Dwarki et al., Meth. Enzymol., 2003, 217: 644-654.*

Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).

Cowling, V., Regulation of mRNA Cap Methylation, Biochemical Journal, 425:295-302 (2010).

Fechter, P. and Brownlee, G.G., Recognition of mRNA Cap Structures by Viral and Cellular Proteins, Journal of General Virology, 86:1239-1249 (2005).

Garbuzenko, O.B. et al., Intratracheal Versus Intravenous Liposomal Delivery of siRNA, Antisense Oligonucleotides and Anticancer Drug, Pharmaceutical Research, 26(2):382-394 (2008).

Higman, M.A. et al., the mRNA (Guanine-7-)methyltransferase Domain of the Vaccinia Virus mRNA Capping Enzyme, The Journal of Biological Chemistry, 269(21):14974-14981 (1994).

Kormann, M.S.D. et al., Expression of Therapeutic Proteins After Delivery of Chemically Modified mRNA in Mice, Nature Biotechnology, 29(2):154-157 (2011) and online methods 2 pages.

Kvasnica, M. et al., Platinum(I) Complexes with Steroidal Esters of L-Methionine and L-Histidine: Synthesis, Characterization and Cytotoxic Activity, Bioorganic & Medicinal Chemistry, 16:3704-3713 (2008).

Li, L. et al., Preparation and Gene Delivery of Alkaline Amino Acids-Based Cationic Liposomes, Archives of Pharmaceutical Research, 31(7):924-931 (2008).

Mansour, H.M. et al., Nanomedicine in Pulmonary Delivery, International Journal of Nanomedicine, 4:299-319 (2009).

Merkel, O.M. and Kissel, T., Nonviral Pulmonary Delivery of siRNA, Accounts of Chemical Research, 1-10 (2011).

Okumura, K. et al., Bax mRNA Therapy Using Cationic Liposomes for Human Malignant Melanoma, The Journal of Gene Medicine, 10:910-917 (2008).

Probst, J. et al., Spontaneous Cellular Uptake of Exogenous Messenger RNA In Vivo is Nucleic Acid-Specific Saturable and Ion Dependent, Gene Therapy, 14:1175-180 (2007).

Rabinovich, P.M. et al., Synthetic Messenger RNA as a Tool for Gene Therapy, Human Gene Therapy, 17:1027-1035 (2006).

(56) References Cited

OTHER PUBLICATIONS

Ratajczak, J. et al., Membrane-Derived Microvesicles: Important and Underappreciated Mediators of Cell-to-Cell Communication, Leukemia, 20:1487-1495 (2006).
Reddy, A. et al., The Effect of Labour and Placental Separation on the Shedding of Syncytiotrophoblast Microparticles, Cell-Free DNA and mRNA in Normal Pregnancy and Pre-Eclampsia, Placenta 29:942-949 (2008).
Schnierle, B.S. et al., Cap-Specific mRNA (Nucleoside-$O^2$-)-Methlytransferase and Poly(A)Polymerase Stimulatory Activities of Vaccinia Virus are Mediated by a Single Protein, Proceedings of the National Academy of Sciences, 89:2897-2901 (1992).
Tavernier, G. et al., mRNA as Gene Therapeutic: How to Control Protein Expression, Journal of Controlled Release, 150:238-247 (2011).
Tendeloo, V.F.V. et al, mRNA-Based Gene Transfer as a Tool for Gene and Cell Therapy, Current Opinion in Molecular Therapeutics, 9(5):423-431 (2007).
Varambally, S. et al., Genomic Loss of MicroRNA-101 Leads to Overexpression of Histone Methyltransferase EZH2 in Cancer, Science, 322:1695-1699 (2008).
Wiehe, J.M. et al., mRNA-Mediated Gene Therapy Delivery into Human Progenitor Cells Promotes Highly Efficient Protein Expression, Journal of Cellular and Molecular Medicine, 11(3):521-530 (2007).
Yamamoto, A. et al., Current Prospects of mRNA Gene Delivery, European Journal of Pharmaceutics and Biopharmaceutics, 71:484-489 (2009).
International Search Report for PCT/US2010/058457, 4 pages (dated May 6, 2011).
Written Opinion for PCT/US2010/058457, 10 pages (dated May 6, 2011).
U.S. Appl. No. 60/083,294.
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-2025 (2003).
Bloomfield, V.A., Quasi-Elastic Light Scattering Applications in Biochemistry and Biology, Ann. Rev. Biophys. Bioeng. 10:421-450 (1981).
Caplen, N.J. et al., In vitro liposome-mediated DNA transfection of epithelial cell lines using the cationic liposome DC-Chol/DOPE, Gene Therapy, 2:603-613 (1995).
Cowling, V.H., Regulation of mRNA cap methylation, Biochemical Journal, 425:295-302 (2010).
Drummond, D.C. et al., Optimizing Liposomes for Delivery of Chemotherapeutic Agents to Solid Tumors, Pharmacological Reviews, 51(4): 691-743 (1999).
Fechter, P. et al., Recognition of mRNA cap structures by viral and cellular proteins, Journal of General Virology, 86:1239-1249 (2005).
Gao, X. et al., A novel cationic liposome reagent for efficient transfection of mammalian cells, Biochemical and Biophysical Research Communications, 179(1):280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Gordon, N. Ornithine transcarbamylase deficiency: a urea cycle defect, European Journal of Paediatric Neurology, 7:115-121 (2003).
Guttman, M. et al., Chromatin signature reveals over a thousand highly conserved large non-coding RNAs in mammals, Nature, 458:223-227 (2009).
Hata, A. et al., Isolation and Characterization of the Human Ornithine Transcarbamylase Gene: Structure of the 5'-End Region, Journal of Biochemistry, 100:717-725 (1986).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Hillery, A.M. et al., Drug Delivery and Targeting for Pharmacists and Pharmaceutical Scientists, Taylor and Francis (2005).

Hope, M.J. et al., Reduction of Liposome Size and Preparation of Unilamellar Vesicles by Extrusion Techniques, In: Liposome Technology, 1:123-139 (1993).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
International Search Report for PCT/US10/58487, 4 pages (dated May 6, 2011).
International Search Report for PCT/US11/62459, 3 pages (dated Apr. 11, 2012).
International Search Report for PCT/US12/41724, 5 pages (dated Oct. 25, 2012).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying *Phaseolus vulgaris* Agglutinin-$L_4$ Isolectin to Malignant Tumors Overexpressing N-Acetylglucosaminyltransferase V, Human Gene Therapy, 19:887-895 (2008).
Klibanov, A.L. et al., Amphipathic polyethyleneglycols effectively prolong the circulation time of liposomes, FEBS, 268(1): 235-237 (1990).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lindgren, V. et al., Human Ornithine Transcarbamylase Locus Mapped to Band Xp21.1 Near the Duchenne Muscular Dystrophy Locus, Science, 226(2675):698-700 (1984).
Liu, Y. et al., Designer Lipids Advance Systemic siRNA Delivery, Molecular Therapy, 18(4):669-670 (2010).
Love, K.T. et al., Lipid-like materials for low-dose, in vivo gene silencing, PNAS, 107(5):1864-1869 (2010).
Malone, R.W., et al., Cationic liposome-mediated RNA transfection, PNAS, 86:6077-6081 (1989).
Merkel, O.M. et al., Nonviral Pulmonary Delivery of siRNA, Accounts of Chemical Research, 10 pages (2011).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Ng, J. et al., LincRNAs join the pluripotency alliance, Nature Genetics, 42:1035-1036 (2010).
Probst, J. et al., Spontaneous cellular uptake of exogenous messenger RNA in vivo is nucleic acid-specific, saturable and ion dependent, Gene Therapy, 14:1175-1180 (2007).

(56) References Cited

OTHER PUBLICATIONS

Reddy, A. et al., The Effect of Labour and Placental Separation on the Shedding of Syncytiotrophoblast Microparticles, Cell-free DNA and mRNA in Normal Pregnancy and Preeclampsia, Placenta, 29:942-949.
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Semple, S.C. et al., Rational design of cationic lipids for siRNA delivery, Nature Biotechnology, 28(2): 172-176 (2010).
Shimada, A. et al., Translocation Pathway of the Intratracheally Instilled Ultrafine Particles from the Lung into the Blood Circulation in the Mouse, Toxicologic Pathology, 34:949-957 (2006).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Suri, M. et al., Genetics for Pediatricians, Remedica Publishing, (2005).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Wiehe, J.M. et al., mRNA-mediated gene delivery into human progenitor cells promotes highly efficient protein expression, Journal of Cellular and Molecular Medicine, 11(3):521-530 (2007).
Wolf, J.A. et al., Protein/Amphipathic Polyamine Complexes Enable Highly Efficient Transfection with Minimal Toxicity, BioTechniques, 23:139-147 (1997).
Written Opinion for PCT/US10/58457, 14 pages (dated May 6, 2011).
Written Opinion for PCT/US11/62459, 9 pages (dated Apr. 11, 2012).
Written Opinion for PCT/US12/41724, 11 pages (dated Oct. 25, 2012).
Yamamoto, A. et al., Current prospects for mRNA gene delivery, European Journal of Pharmaceutics and Biopharmaceutics, 71:484-489 (2009).
Yokoe, H. et al., Spatial dynamics of GFP-tagged proteins investigated by local fluorescence enhancement, Nature Biotechnology, 14(10):1252-1256 (1996).
Chiou, H.C. et al., Enhanced resistance to nuclease degradation of nucleic acids complexed to asialoglycoprotein-polylysine carriers, Nucleic Acids Research, 22(24):5439-5446 (1994).
Elton, C., The Next Next Big Thing, Boston Magazine, pp. 106-118 (Mar. 2013).
Emlen, W. et al., Effect of DNA size and strandedness on the in vivo clearance and organ localization of DNA, Clinical & Experimental Immunology, 56:185-192 (1984).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-92 (2004).
Harada-Shiba, M. et al., Polyion complex micelles as vectors in gene therapy—pharmacokinetics and in vivo; gene transfer, Gene Therapy, 9(6):407-14 (2002).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Maeda-Mamiya, R. et al.,. In vivo gene delivery by cationic tetraamino; fullerene. Proceedings of National Academy of Sciences U S A, 107(12):5339-44 (2010).
Melton, D.A. et al., Efficient in vitro synthesis of biologically active RNA and RNA hybridization probes from; plasmids containing a bacteriophage SP6 promoter, Nucleic Acids Research, 12(18):7035-56 (1984).
Tagawa, M. et al., Gene expression and active virus replication in the liver after injection of duck hepatitis B virus DNA into the peripheral vein of ducklings, Journal of Hepatology, 24:328-334 (1996).
Tsui, N.B. et al., Stability of endogenous and added RNA in blood specimens, serum, and plasma, Clinical Chemistry, 48(10):1647-53 (2002).
Tuschl, T. et al., Targeted mRNA degradation by double-stranded RNA in vitro, Genes and Development, 13(24):3191-7 (1999).
Estimated Number of Animal and Plant Species on Earth, http://www.factmonster.com/ipka/A0934288.html, 2000-2014, 3 pages, (Retrieved Aug. 2, 2014).
Fumoto et al., Targeted Gene Delivery: Importance of Administration Routes, Novel Gene Therapy Approaches, 3-31 (2013).
Haskins, Gene Therapy for Lysosomal Storage Disorders (LDSs) in Large Animal Models, ILAR J., 50(2): 112-121 (2009).
Hess et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy: CII, 55(6): 672-83 (2006).
Hoerr et al., In Vivo Application of RNA Leads to Induction of Specific Cytotoxic T Lymphocytes and Antibodies, European Journal of Immunology, 30(1): 1-7 (2000).
Lorenzi et al., Intranasal Vaccination with Messenger RNA as a New Approach in Gene Therapy: Use Against Tuberculosis, BMC Biotechnology, 10:77: 1-11 (2010).
Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).
Martinon et al., Induction of Virus-Specific Cytotoxic T Lymphocytes in Vivo by Liposome-Entrapped mRNA, European Journal of Immunology, 23(7): 1719-22 (1993).
Yasuda et al., Fabry Disease: Novel [alpha]-Galactosidase A 3-terminal Mutations Result in Multiple Transcripts Due to Aberrant 3-End Formation, American Journal of Human Genetics, 73: 162-73 (2003).

\* cited by examiner
† cited by third party

LIVER SPECIFIC DELIVERY OF MESSENGER RNA

CROSS REFERENCE TO RELATED APPLICATIONS

This patent application is a divisional of U.S. patent application Ser. No. 12/957,340 filed on Nov. 30, 2010, which claims the benefit of U.S. Provisional Patent Application Ser. No. 61/265,653, filed Dec. 1, 2009, the entirety of each of which is incorporated herein by reference.

SEQUENCE LISTING

The present specification makes reference to a Sequence Listing (submitted electronically as a .txt file named "Sequence Listing.txt on Mar. 13, 2013). The .txt file was generated on Mar. 13, 2013 and is 3.18 kb in size. The entire contents of the Sequence Listing are herein incorporated by reference.

BACKGROUND OF THE INVENTION

Novel approaches and therapies are still needed for the treatment of protein and enzyme deficiencies, particularly strategies and therapies which overcome the challenges and limitations associated with the administration of nucleic acids and the transfection of target cells. Additional approaches which modulate or supplement the expression of a deficient protein or enzyme and thus ameliorate the underlying deficiency would be useful in the development of appropriate therapies for associated disorders.

For example, the urea cycle metabolic disorders represent protein and enzyme deficiencies for which there are no currently available cures. The urea cycle is a series of biochemical reactions which occurs in many animals that produce urea ($(NH_2)_2CO$) from ammonia ($NH_3$) and, in mammals, takes place only in the liver. Specifically, the urea cycle consists of a series of five biochemical reactions and serves two primary functions: the elimination of nitrogen as urea and the synthesis of arginine. Defects in the urea cycle result in the accumulation of ammonia and its precursor amino acids (glutamine, glutamic acid, aspartic acid, and glycine). The resulting high levels of ammonia are neurotoxic, and the triad of hyperammonemia, encephalopathy, and respiratory alkalosis characterizes the urea cycle disorders.

Ornithine transcarbamylase (OTC) deficiency represents one such urea cycle genetic disorder. Typically, a subject with OTC deficiency has a reduced level of the enzyme OTC. In the classic severe form of OTC deficiency, within the first days of life patients present with lethargy, convulsions, coma and severe hyperammonemia that quickly lead to a deteriorating and fatal outcome absent appropriate medical intervention. If left untreated, complications from OTC deficiency may include developmental delay, mental retardation and/or death.

Treatment of OTC deficient patients primarily involves the regulation of serum ammonia and hemodialysis remains the only effective means to rapidly lower serum ammonia levels. Generally, the treatment goal of urea cycle metabolic disorders is to provide sufficient protein and arginine for growth, development, and energy while preventing the development of hyperammonemia and hyperglutaminemia. Therapeutic approaches that are currently available for the therapeutic management of urea cycle metabolic disorders such as OTC deficiency rely heavily upon dietary management. There are no currently available long-term treatments or cures for urea cycle metabolic disorders. Novel therapies that increase the level or production of an affected protein or enzyme in target cells, such as hepatocytes, or that modulate the expression of nucleic acids encoding the affected protein or enzyme could provide a treatment or even a cure for metabolic disorders, including metabolic disorders such as OTC deficiency.

SUMMARY OF THE INVENTION

Disclosed are methods of intracellular delivery of nucleic acids that are capable of correcting existing genetic defects and/or providing beneficial functions to one or more target cells. Following successful delivery to target tissues and cells, the compositions and nucleic acids of the present invention transfect that target cell and the nucleic acids (e.g., mRNA) can be translated into the gene product of interest (e.g., a functional protein or enzyme) or can otherwise modulate or regulate the presence or expression of the gene product of interest.

The compositions and methods provided herein are useful in the management and treatment of a large number of diseases, in particular diseases which result from protein and/or enzyme deficiencies. Individuals suffering from such diseases may have underlying genetic defects that lead to the compromised expression of a protein or enzyme, including, for example, the non-synthesis of the protein, the reduced synthesis of the protein, or synthesis of a protein lacking or having diminished biological activity. In particular, the methods and compositions provided herein are useful for the treatment of the urea cycle metabolic disorders that occur as a result of one or more defects in the biosynthesis of enzymes involved in the urea cycle. The methods and compositions provided herein are also useful in various in vitro and in vivo applications in which the delivery of a nucleic acid (e.g., mRNA) to a target cell and transfection of that target cell are desired.

In one embodiment, the compositions provided herein may comprise a nucleic acid, a transfer vehicle and an agent to facilitate contact with, and subsequent transfection of a target cell. The nucleic acid can encode a clinically useful gene product or protein. For example, the nucleic acid may encode a functional urea cycle enzyme. In preferred embodiments, the nucleic acid is RNA, or more preferably mRNA encoding a functional protein or enzyme.

In some embodiments, compositions and methods for increasing expression of a functional protein or enzyme in a target cell are provided. For example, the compositions and methods provided herein may be used to increase the expression of a urea cycle enzyme (e.g., OTC, CPS1, ASS1, ASL or ARG1). In some embodiments, the composition comprises an mRNA and a transfer vehicle. In some embodiments, the mRNA encodes a urea cycle enzyme. In some embodiments the mRNA can comprise one or more modifications that confer stability to the mRNA (e.g., compared to a wild-type or native version of the mRNA) and may also comprise one or more modifications relative to the wild-type which correct a defect implicated in the associated aberrant expression of the protein. For example, the nucleic acids of the present invention may comprise modifications to one or both the 5' and 3' untranslated regions. Such modifications may include, but are not limited to, the inclusion of a partial sequence of a cytomegalovirus (CMV) immediate-early 1 (IE1) gene, a poly A tail, a Cap1 structure or a sequence encoding human growth hormone (hGH).

Methods of treating a subject, wherein the subject has a protein or enzyme deficiency are also provided. The methods can comprise administering a composition provided herein. For example, methods of treating or preventing conditions in which production of a particular protein and/or utilization of a particular protein is inadequate or compromised are provided. In one embodiment, the methods provided herein can be used to treat a subject having a deficiency in one or more urea cycle enzymes. The method can comprise contacting and transfecting target cells or tissues (such as hepatocytes that are deficient in one or more urea cycle enzymes) with a composition provided herein, wherein the nucleic acid encodes the deficient urea cycle enzyme. In this manner, the expression of the deficient enzyme in the target cell is increased, which in turn is expected to ameliorate the effects of the underlying enzyme deficiency. The protein or enzyme expressed by the target cell from the translated mRNA may be retained within the cytosol of the target cell or alternatively may be secreted extracellularly. In some embodiments, the nucleic acid is an mRNA. In some embodiments, the mRNA comprises a modification that confers stability to the mRNA code (e.g., when compared to the wild-type or native version of the mRNA). For example, the mRNA encoding a functional enzyme may comprise one or more modifications to one or both the 5' and 3' untranslated regions.

In a preferred embodiment, the nucleic acids (e.g., mRNA) provided herein are formulated in a lipid or liposomal transfer vehicle to facilitate delivery to the target cells and/or to stabilize the nucleic acids contained therein. Contemplated transfer vehicles may comprise one or more cationic lipids, non-cationic lipids, and/or PEG-modified lipids. For example, the transfer vehicle may comprise a mixture of the lipids CHOL, DOPE, IThinDMA and DMG-PEG-2000. In another embodiment, the transfer vehicle may comprise the lipids ICE, DOPE and DMG-PEG-2000. In still another embodiment the transfer vehicle may comprise one or more lipids selected from the group consisting of ICE, DSPC, CHOL, DODAP, DOTAP and C8-PEG-2000 ceramide. In a preferred embodiment, the transfer vehicle is a liposome or a lipid nanoparticle which is capable of preferentially distributing to the target cells and tissues in vivo.

Methods of expressing a functional protein or enzyme (e.g., a urea cycle enzyme) in a target cell are also provided. In some embodiments, the target cell is deficient in a urea cycle enzyme. The methods comprise contacting the target cell with a composition comprising an mRNA and a transfer vehicle. Following expression of the protein or enzyme encoded by the mRNA, the expressed protein or enzyme may be retained within the cytosol of the target cell or alternatively may be secreted extracellularly. In some embodiments, the mRNA encodes a urea cycle enzyme. In some embodiments the mRNA can comprise one or more modifications that confer stability to the mRNA and may also comprise one or more modifications relative to the wild-type that correct a defect implicated in the associated aberrant expression of the protein. In some embodiments, the compositions and methods of the present invention rely on the target cells to express the functional protein or enzyme encoded by the exogenously administered nucleic acid (e.g., mRNA). Because the protein or enzyme encoded by the exogenous mRNA are translated by the target cell, the proteins and enzymes expressed may be characterized as being less immunogenic relative to their recombinantly prepared counterparts.

Also provided are compositions and methods useful for facilitating the transfection and delivery of one or more nucleic acids (e.g., mRNA) to target cells. For example, the compositions and methods of the present invention contemplate the use of targeting ligands capable of enhancing the affinity of the composition to one or more target cells. In one embodiment, the targeting ligand is apolipoprotein-B or apolipoprotein-E and corresponding target cells express low-density lipoprotein receptors, thereby facilitating recognition of the targeting ligand. The methods and compositions of the present invention may be used to preferentially target a vast number of target cells. For example, contemplated target cells include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

DETAILED DESCRIPTION OF THE INVENTION

Figure 1:
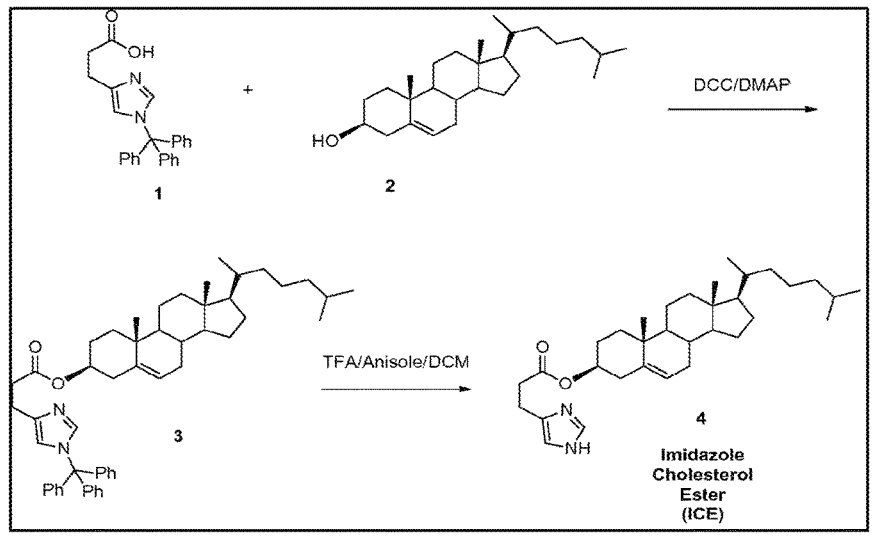
FIG. 1 illustrates the synthesis of the imidazole cholesterol ester lipid ICE.

Disclosed herein are compositions that facilitate the delivery of nucleic acids to, and the subsequent transfection of, target cells. In particular, the compositions provided herein are useful for the treatment of diseases which result from the deficient production of proteins and/or enzymes. For example, suitable diseases that may be treated are those in which a genetic mutation in a particular gene causes affected cells to not express, have reduced expression of, or to express a non-functional product of that gene. Contacting such target cells with the compositions of the present invention such that the target cells are transfected with a nucleic acid encoding a functional version of the gene product allows the production of a functional protein or enzyme product this is useful in the treatment of such deficiency.

Provided herein are compositions for modulating the expression of a protein in a target cell. In some embodiments, the composition comprises an RNA molecule and a transfer vehicle. Compositions for increasing expression of a urea cycle enzyme in a target cell are also provided. The compositions comprise, for example, an mRNA and a transfer vehicle. The mRNA encodes, for example, a functional urea cycle enzyme. In some embodiments, the mRNA of the composition can be modified to impart enhanced stability (e.g., relative to the wild-type version of the mRNA and/or the version of the mRNA found endogenously in the target cell). For example, the mRNA of the composition can include a modification compared to a wild-type version of the mRNA, wherein the modification confers stability to the mRNA of the composition.

Methods of expressing a urea cycle enzyme in a target cell are provided. In some embodiments, the target cell is deficient in a urea cycle enzyme. The methods provided herein comprise contacting the target cell with a composition comprising an mRNA and a transfer vehicle, wherein the mRNA encodes one or more urea cycle enzymes. In some embodiments, the mRNA of the composition is more stable than the wild-type version of the mRNA and/or more stable than the version of the mRNA found endogenously in the target cell.

Methods of treating a subject with a urea cycle deficiency are provided. The methods comprise administering a composition comprising an mRNA and a transfer vehicle, wherein the mRNA encodes a urea cycle enzyme. In some embodiments, the mRNA of the composition is more stable than the wild-type version of the mRNA and/or more stable than the version of the mRNA found endogenously in the target.

Provided herein are methods of and compositions for modulating the level of mRNA and/or the expression of proteins. In some embodiments, the compositions provided herein are capable of modulating the expression of a particular protein by decreasing expression of mRNA encoding that protein in a target cell or tissue. For example, in one embodiment, the composition comprises a miRNA or a nucleic acid encoding miRNA where the miRNA is capable of reducing or eliminating expression of a particular mRNA in a target cell. In some embodiments, the nucleic acid of the composition is more stable (e.g., limited nuclease susceptibility) compared to a wild-type and/or endogenous version of the nucleic acid.

As used herein, the term "nucleic acid" refers to genetic material (e.g., oligonucleotides or polynucleotides comprising DNA or RNA). In some embodiments, the nucleic acid of the compositions is RNA. Suitable RNA includes mRNA, siRNA, miRNA, snRNA and snoRNA. Contemplated nucleic acids also include large intergenic non-coding RNA (lincRNA), which generally do not encode proteins, but rather function, for example, in immune signaling, stem cell biology and the development of disease. (See, e.g., Guttman, et al., 458: 223-227 (2009); and Ng, et al., Nature Genetics 42: 1035-1036 (2010), the contents of which are incorporated herein by reference). In a preferred embodiment, the nucleic acids of the invention include RNA or stabilized RNA encoding a protein or enzyme. The present invention contemplates the use of such nucleic acids (and in particular RNA or stabilized RNA) as a therapeutic capable of facilitating the expression of a functional enzyme or protein, and preferably the expression of a functional enzyme of protein in which a subject is deficient (e.g., a urea cycle enzyme). The term "functional", as used herein to qualify a protein or enzyme, means that the protein or enzyme has biological activity, or alternatively is able to perform the same, or a similar function as the native or normally-functioning protein or enzyme. The subject nucleic acid compositions of the present invention are useful for the treatment of a various metabolic or genetic disorders, and in particular those genetic or metabolic disorders which involve the non-expression, misexpression or deficiency of a protein or enzyme.

In the context of the present invention the term "expression" is used in its broadest sense to refer to either the transcription of a specific gene or nucleic acid into at least one mRNA transcript, or the translation of at least one mRNA or nucleic acid into a protein or enzyme. For example, contemplated by the present invention are compositions which comprise one or more mRNA nucleic acids which encode functional proteins or enzymes, and in the context of such mRNA nucleic acids, the term expression refers to the translation of such mRNA to produce the protein or enzyme encoded thereby.

The nucleic acids provided herein can be introduced into cells or tissues of interest. In some embodiments, the nucleic acid is capable of being expressed (e.g., the transcription of mRNA from a gene), translated (e.g., the translation of the encoded protein or enzyme from a synthetic or exogenous mRNA transcript) or otherwise capable of conferring a beneficial property to the target cells or tissues (e.g., reducing the expression of a target nucleic acid or gene). The nucleic acid may encode, for example, a hormone, enzyme, receptor, polypeptide, peptide or other protein of interest. A nucleic acid may also encode a small interfering RNA (siRNA) or antisense RNA for the purpose of decreasing or eliminating expression of an endogenous nucleic acid or gene. In one embodiment of the present invention, the nucleic acid (e.g., mRNA encoding a deficient protein or enzyme) may optionally have chemical or biological modifications which, for example, improve the stability and/or half-life of such nucleic acid or which improve or otherwise facilitate translation.

The nucleic acids of the present invention may be natural or recombinant in nature and may exert their therapeutic activity using either sense or antisense mechanisms of action.

Also contemplated by the present invention is the co-delivery of one or more unique nucleic acids to target cells, for example, by combining two unique nucleic acids into a single transfer vehicle. In one embodiment of the present invention, a therapeutic first nucleic acid, such as mRNA encoding galactose-1-phosphate uridyltransferase (GALT), and a therapeutic second nucleic acid, such as mRNA encoding galatokinase (GALK), may be formulated in a single transfer vehicle and administered (e.g., for the treatment of galactosemia). The present invention also contemplates co-delivery and/or co-administration of a therapeutic first nucleic acid and a second nucleic acid to facilitate and/or enhance the function or delivery of the therapeutic first nucleic acid. For example, such a second nucleic acid (e.g., exogenous or synthetic mRNA) may encode a membrane transporter protein that upon expression (e.g., translation of the exogenous or synthetic mRNA) facilitates the delivery or enhances the biological activity of the first nucleic acid. Alternatively, the therapeutic first nucleic acid may be administered with a second nucleic acid that functions as a "chaperone" for example, to direct the folding of either the therapeutic first nucleic acid or endogenous nucleic acids.

Also contemplated is the delivery of one or more therapeutic nucleic acids to treat a single disorder or deficiency, wherein each such therapeutic nucleic acid functions by a different mechanism of action. For example, the compositions of the present invention may comprise a therapeutic first nucleic acid which, for example, is administered to correct an endogenous protein or enzyme deficiency, and which is accompanied by a second nucleic acid, which is administered to deactivate or "knock-down" a malfunctioning endogenous nucleic acid and its protein or enzyme product. Such nucleic acids may encode, for example mRNA and siRNA.

While in vitro transcribed nucleic acids (e.g., mRNA) may be transfected into target cells, such nucleic acids are readily and efficiently degraded by the cell in vivo, thus rendering such nucleic acids ineffective. Moreover, some nucleic acids are unstable in bodily fluids (particularly human serum) and can be degraded even before reaching a target cell. In addition, within a cell, a natural mRNA can decay with a half-life of between 30 minutes and several days.

The nucleic acids provided herein, and in particular the mRNA nucleic acids provided herein, preferably retain at least some ability to be translated, thereby producing a functional protein or enzyme within a target cell. Accordingly, the present invention relates to the administration of a stabilized nucleic acid (e.g., mRNA which has been stabilized against in vivo nuclease digestion or degradation) to modulate the expression of a gene or the translation of a functional enzyme or protein within a target cell. In a preferred embodiment of the present invention, the activity of the nucleic acid (e.g., mRNA encoding a functional protein or enzyme) is prolonged over an extended period of time. For example, the activity of the nucleic acids may be prolonged such that the compositions of the present invention are administered to a subject on a semi-weekly or bi-weekly basis, or more preferably on a monthly, bi-monthly, quarterly or an annual basis. The extended or prolonged activity of the compositions of the present invention, and in particular of the mRNA comprised therein, is directly related to the quantity of functional protein or enzyme translated from such mRNA. Similarly, the activity of the compositions of the present invention may be further extended or prolonged by modifications made to improve or enhance translation of the mRNA nucleic acids. For example, the Kozac consensus sequence plays a role in the initiation of protein translation, and the inclusion of such a Kozac consensus sequence in the mRNA nucleic acids of the present invention may further extend or prolong the activity of the mRNA nucleic acids. Furthermore, the quantity of functional protein or enzyme translated by the target cell is a function of the quantity of nucleic acid (e.g., mRNA) delivered to the target cells and the stability of such nucleic acid. To the extent that the stability of the nucleic acids of the present invention may be improved or enhanced, the half-life, the activity of the translated protein or enzyme and the dosing frequency of the composition may be further extended.

Accordingly, in a preferred embodiment, the nucleic acids provided herein comprise at least one modification which confers increased or enhanced stability to the nucleic acid, including, for example, improved resistance to nuclease digestion in vivo. As used herein, the terms "modification" and "modified" as such terms relate to the nucleic acids provided herein, include at least one alteration which preferably enhances stability and renders the nucleic acid more stable (e.g., resistant to nuclease digestion) than the wild-type or naturally occurring version of the nucleic acid. As used herein, the terms "stable" and "stability" as such terms relate to the nucleic acids of the present invention, and particularly with respect to the mRNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or conditions within the target cell or tissue, thereby increasing or enhancing the residence of such nucleic acids in the target cell, tissue, subject and/or cytoplasm. The stabilized nucleic acid molecules provided herein demonstrate longer half-lives relative to their naturally occurring, unmodified counterparts (e.g. the wild-type version of the nucleic acid). Also contemplated by the terms "modification" and "modified" as such terms related to the nucleic acids of the present invention are alterations which improve or enhance translation of mRNA nucleic acids, including for example, the inclusion of sequences which function in the initiation of protein translation (e.g., the Kozac consensus sequence). (Kozak, M., Nucleic Acids Res 15 (20): 8125-48 (1987)).

In some embodiments, the nucleic acids of the present invention have undergone a chemical or biological modification to render them more stable. Exemplary modifications to a nucleic acid include the depletion of a base (e.g., by deletion or by the substitution of one nucleotide for another) or modification of a base, for example, the chemical modification of a base. The phrase "chemical modifications" as used herein, includes modifications which introduce chemistries which differ from those seen in naturally occurring nucleic acids, for example, covalent modifications such as the introduction of modified nucleotides, (e.g., nucleotide analogs, or the inclusion of pendant groups which are not naturally found in such nucleic acid molecules).

In addition, suitable modifications include alterations in one or more nucleotides of a codon such that the codon encodes the same amino acid but is more stable than the codon found in the wild-type version of the nucleic acid. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In a another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudouridines. The incorporation of pseudouridines into the mRNA nucleic acids of the present invention may enhance stability and translational capacity, as well as diminishing immunogenicity in vivo. (See, e.g., Kariko, K., et al., Molecular Therapy 16 (11): 1833-1840 (2008)). Substitutions and modifications to the nucleic acids of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The term modification also includes, for example, the incorporation of non-nucleotide linkages or modified nucleotides into the nucleic acid sequences of the present invention (e.g., modifications to one or both the 3' and 5' ends of an mRNA molecule encoding a functional protein or enzyme). Such modifications include the addition of bases to a nucleic acid sequence (e.g., the inclusion of a poly A tail or a longer poly A tail), the alteration of the 3' UTR or the 5' UTR, complexing the nucleic acid with an agent (e.g., a protein or a complementary nucleic acid molecule), and inclusion of elements which change the structure of a nucleic acid molecule (e.g., which form secondary structures).

The poly A tail is thought to stabilize natural messengers and synthetic sense RNA. Therefore, in one embodiment a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In one embodiment, the length of the poly A tail is at least about 90, 200, 300, 400 at least 500 nucleotides. In one embodiment, the length of the poly A tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of protein expression in a cell. In one embodiment, the stabilized nucleic acid molecules are sufficiently resistant to in vivo degradation (e.g., by nucleases), such that they may be delivered to the target cell without a transfer vehicle.

In one embodiment, a nucleic acid encoding a protein can be modified by the incorporation 3' and/or 5' untranslated (UTR) sequences which are not naturally found in the wild-type nucleic acid. In one embodiment, 3' and/or 5' flanking sequence which naturally flanks an mRNA and encodes a second, unrelated protein can be incorporated into the nucleotide sequence of an mRNA molecule encoding a therapeutic or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA nucleic acid molecule to increase the stability of the sense mRNA molecule.

Also contemplated by the present invention are modifications to the nucleic acid sequences made to one or both of the 3' and 5' ends of the nucleic acid. For example, the present invention contemplates modifications to the 5' end of the nucleic acids (e.g., mRNA) to include a partial sequence of a CMV immediate-early 1 (IE1) gene, or a fragment thereof (e.g., SEQ ID NO: 2) to improve the nuclease resistance and/or improve the half-life of the nucleic acid. In addition to increasing the stability of the mRNA nucleic acid sequence, it has been surprisingly discovered the inclusion of a partial sequence of a CMV immediate-early 1 (IE1) gene enhances the translation of the mRNA and the expression of the functional protein or enzyme. Also contemplated is the inclusion of a sequence encoding human growth hormone (hGH), or a fragment thereof (e.g., SEQ ID NO: 3) to one or both of the 3' and 5' ends of the nucleic acid (e.g., mRNA) to further stabilize the nucleic acid. Generally, preferred modifications improve the stability and/or pharmacokinetic properties (e.g., half-life) of the nucleic acid relative to their unmodified counterparts, and include, for example modifications made to improve such nucleic acid's resistance to in vivo nuclease digestion.

In some embodiments, the composition can comprise a stabilizing reagent. The compositions can include one or more formulation reagents that bind directly or indirectly to, and stabilize the nucleic acid, thereby enhancing residence time in the cytoplasm of a target cell. Such reagents preferably lead to an improved half-life of a nucleic acid in the target cells. For example, the stability of an mRNA and efficiency of translation may be increased by the incorporation of "stabilizing reagents" that form complexes with the nucleic acids (e.g., mRNA) that naturally occur within a cell (see e.g., U.S. Pat. No. 5,677,124). Incorporation of a stabilizing reagent can be accomplished for example, by combining the poly A and a protein with the mRNA to be stabilized in vitro before loading or encapsulating the mRNA within a transfer vehicle. Exemplary stabilizing reagents include one or more proteins, peptides, aptamers, translational accessory protein, mRNA binding proteins, and/or translation initiation factors.

Stabilization of the compositions may also be improved by the use of opsonization-inhibiting moieties, which are typically large hydrophilic polymers that are chemically or physically bound to the transfer vehicle (e.g., by the intercalation of a lipid-soluble anchor into the membrane itself, or by binding directly to active groups of membrane lipids). These opsonization-inhibiting hydrophilic polymers form a protective surface layer which significantly decreases the uptake of the liposomes by the macrophage-monocyte system and reticulo-endothelial system (e.g., as described in U.S. Pat. No. 4,920,016, the entire disclosure of which is herein incorporated by reference). Transfer vehicles modified with opsonization-inhibition moieties thus remain in the circulation much longer than their unmodified counterparts.

When RNA is hybridized to a complementary nucleic acid molecule (e.g., DNA or RNA) it may be protected from nucleases. (Krieg, et al. Melton. Methods in Enzymology. 1987; 155, 397-415). The stability of hybridized mRNA is likely due to the inherent single strand specificity of most RNases. In some embodiments, the stabilizing reagent selected to complex a nucleic acid is a eukaryotic protein, (e.g., a mammalian protein). In yet another embodiment, the nucleic acid molecule (e.g., mRNA) for use in sense therapy can be modified by hybridization to a second nucleic acid molecule. If an entire mRNA molecule were hybridized to a complementary nucleic acid molecule translation initiation may be reduced. In some embodiments the 5' untranslated region and the AUG start region of the mRNA molecule may optionally be left unhybridized. Following translation initiation, the unwinding activity of the ribosome complex can function even on high affinity duplexes so that translation can proceed. (Liebhaber. J. Mol. Biol. 1992; 226: 2-13; Monia, et al. J Biol Chem. 1993; 268: 14514-22.)

It will be understood that any of the above described methods for enhancing the stability of nucleic acids may be used either alone or in combination with one or more of any of the other above-described methods and/or compositions.

In one embodiment, the compositions of the present invention facilitate the delivery of nucleic acids to target cells. In some embodiments, facilitating delivery to target cells includes increasing the amount of nucleic acid that comes in contact with the target cells. In some embodiments, facilitating delivery to target cells includes reducing the amount of nucleic acid that comes into contact with non-target cells. In some embodiments, facilitating delivery to target cells includes allowing the transfection of at least some target cells with the nucleic acid. In some embodiments, the level of expression of the product encoded by the delivered nucleic acid is increased in target cells.

The nucleic acids of the present invention may be optionally combined with a reporter gene (e.g., upstream or downstream of the coding region of the nucleic acid) which, for example, facilitates the determination of nucleic acid delivery to the target cells or tissues. Suitable reporter genes may include, for example, Green Fluorescent Protein mRNA (GFP mRNA), Renilla Luciferase mRNA (Luciferase mRNA), Firefly Luciferase mRNA, or any combinations thereof. For example, GFP mRNA may be fused with a nucleic acid encoding OTC mRNA to facilitate confirmation of mRNA localization in the target cells, tissues or organs.

As used herein, the terms "transfect" or "transfection" mean the intracellular introduction of a nucleic acid into a cell, or preferably into a target cell. The introduced nucleic acid may be stably or transiently maintained in the target cell. The term "transfection efficiency" refers to the relative amount of nucleic acid up-taken by the target cell which is subject to transfection. In practice, transfection efficiency is estimated by the amount of a reporter nucleic acid product expressed by the target cells following transfection. Preferred are compositions with high transfection efficacies and in particular those compositions that minimize adverse effects which are mediated by transfection of non-target cells and tissues. The compositions of the present invention that demonstrate high transfection efficacies improve the likelihood that appropriate dosages of the nucleic acid will be delivered to the site of pathology, while minimizing potential systemic adverse effects.

As provided herein, the compositions can include a transfer vehicle. As used herein, the term "transfer vehicle" includes any of the standard pharmaceutical carriers, diluents, excipients and the like which are generally intended for use in connection with the administration of biologically active agents, including nucleic acids. The compositions and in particular the transfer vehicles described herein are capable of delivering nucleic acids of varying sizes to their target cells or tissues. In one embodiment of the present invention, the transfer vehicles of the present invention are capable of delivering large nucleic acid sequences (e.g., nucleic acids of at least 1 kDa, 1.5 kDa, 2 kDa, 2.5 kDa, 5 kDa, 10 kDa, 12 kDa, 15 kDa, 20 kDa, 25 kDa, 30 kDa, or more). The nucleic acids can be formulated with one or more acceptable reagents, which provide a vehicle for delivering such nucleic acids to target cells. Appropriate reagents are generally selected with regards to a number of factors, which include, among other things, the biological or chemical properties of the nucleic acids (e.g., charge), the intended route of administration, the anticipated biological environment to which such nucleic acids will be exposed and the specific properties of the intended target cells. In some embodiments, transfer vehicles, such as liposomes, encapsulate the nucleic acids without compromising biological activity. In some embodiments, the transfer vehicle demonstrates preferential and/or substantial binding to a target cell relative to non-target cells. In a preferred embodiment, the transfer vehicle delivers its contents to the target cell such that the nucleic acids are delivered to the appropriate subcellular compartment, such as the cytoplasm.

In some embodiments, the transfer vehicle is a liposomal vesicle, or other means to facilitate the transfer of a nucleic acid to target cells and tissues. Suitable transfer vehicles include, but are not limited to, liposomes, nanoliposomes, ceramide-containing nanoliposomes, proteoliposomes, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95). In a preferred embodiment of the present invention, the transfer vehicle is formulated as a lipid nanoparticle. As used herein, the phrase "lipid nanoparticle" refers to a transfer vehicle comprising one or more lipids (e.g., cationic and/or non-cationic lipids). Preferably, the lipid nanoparticles are formulated to deliver one or more nucleic acids (e.g., mRNA) to one or more target cells or tissues. The use of lipids, either alone or as a component of the transfer vehicle, and in particular lipid nanoparticles, is preferred. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. In one embodiment, the transfer vehicle is selected based upon its ability to facilitate the transfection of a nucleic acid to a target cell.

In one embodiment of the present invention, the transfer vehicle may be selected and/or prepared to optimize delivery of the nucleic acid to the target cell, tissue or organ. For example, if the target cell is a hepatocyte the properties of the transfer vehicle (e.g., size, charge and/or pH) may be optimized to effectively deliver such transfer vehicle to the target cell or organ, reduce immune clearance and/or promote retention in that target organ. Alternatively, if the target tissue is the central nervous system (e.g., mRNA administered for the treatment of neurodegenerative diseases may specifically target brain or spinal tissue) selection and preparation of the transfer vehicle must consider penetration of, and retention within the blood brain barrier and/or the use of alternate means of directly delivering such transfer vehicle to such target tissue. In one embodiment, the compositions of the present invention may be combined with agents that facilitate the transfer of exogenous nucleic acids (e.g., agents which disrupt or improve the permeability of the blood brain barrier and thereby enhance the transfer of exogenous mRNA to the target cells).

The use of liposomal transfer vehicles to facilitate the delivery of nucleic acids to target cells is contemplated by the present invention. Liposomes (e.g., liposomal lipid nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.).

In the context of the present invention, a liposomal transfer vehicle typically serves to transport the nucleic acid to the target cell. For the purposes of the present invention, the liposomal transfer vehicles, are prepared to contain the desired nucleic acids. The process of incorporation of a desired entity (e.g., a nucleic acid) into a liposome is often referred to as "loading" (Lasic, et al., FEBS Lett., 312: 255-258, 1992). The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome.

The purpose of incorporating a nucleic acid into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in a preferred embodiment of the present invention, the selected transfer vehicle is capable of enhancing the stability of the nucleic acid(s) (e.g., mRNA encoding a functional protein) contained therein. The liposome can allow the encapsulated nucleic acid to reach the target cell and/or may preferentially allow the encapsulated nucleic acid to reach the target cell, or alternatively limit the delivery of such nucleic acids to other sites or cells where the presence of the administered nucleic acid may be useless or undesirable. Furthermore, incorporating the nucleic acids into, a transfer vehicle, such as for example, a cationic liposome, also facilitates the delivery of such nucleic acids into a target cell.

Ideally, liposomal transfer vehicles are prepared to encapsulate one or more desired nucleic acids (e.g., mRNA encoding a urea cycle enzyme) such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28 fold in a number of cell lines both in vitro and in vivo. (See N. J. Caplen, et al., Gene Ther. 1995; 2: 603; S. Li, et al., Gene Ther. 1997; 4, 891.)

The present invention contemplates the use of cationic lipids and liposomes to encapsulate and/or enhance the delivery of nucleic acids into their target cells and tissues. As used herein, the phrase "cationic lipid" refers to any of a number of lipid species that carry a net positive charge at a selected pH, such as physiological pH. The contemplated liposomal transfer vehicles and lipid nanoparticles may be prepared by including multi-component lipid mixtures of varying ratios employing one or more cationic lipids, non-cationic lipids and PEG-modified lipids. Several cationic lipids have been described in the literature, many of which are commercially available. In some embodiments, the cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with dioleoylphosphatidylethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. No. 5,171,678; U.S. Pat. No. 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-oc-tadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl-[1,3]-dioxolane or "DLin-K-XTC2-DMA", or mixtures thereof (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335).

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000. (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids, for example, the imidazole cholesterol ester or "ICE" lipid (3S,10R,13R,17R)-10,13-dimethyl-17-(R)-6-methylheptan-2-yl)-2,3,4,7,8,9,10,11,12,13,14,15,16,17-tetradecahydro-1H-cyclopenta[a]phenanthren-3-yl3-(1H-imidazol-4-yl)propanoate, as represented by structure (I) below. In a preferred embodiment, a transfer vehicle (e.g., a lipid nanoparticle) for delivery of RNA (e.g., mRNA) or protein (e.g., an enzyme), for example a therapeutic amount of RNA or protein, may comprise one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl3-(1H-imidazol-4-yl)propanoate, as represented by structure (I).

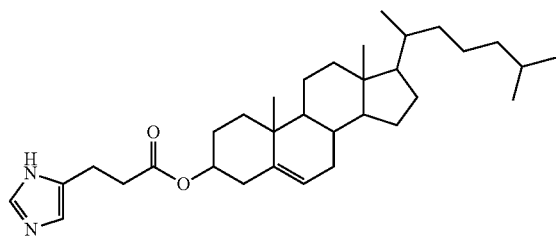

(I)

Without wishing to be bound by a particular theory, it is believed that the fusogenicity of the imidazole-based cationic lipid ICE is related to the endosomal disruption which is facilitated by the imidazole group, which has a lower pKa relative to traditional cationic lipids. The endosomal disruption in turn promotes osmotic swelling and the disruption of the liposomal membrane, followed by the transfection or intracellular release of the nucleic acid(s) contents loaded therein into the target cell. The imidazole-based cationic lipids are also characterized by their reduced toxicity relative to other cationic lipids. The imidazole-based cationic lipids (e.g., ICE) may be used as the sole cationic lipid in the transfer vehicle or lipid nanoparticle, or alternatively may be combined with traditional cationic lipids (e.g., DOPE, DC-Chol), non-cationic lipids, PEG-modified lipids and/or helper lipids. The cationic lipid may comprise a molar ratio of about 1% to about 90%, about 2% to about 70%, about 5% to about 50%, about 10% to about 40% of the total lipid present in the transfer vehicle, or preferably about 20% to about 70% of the total lipid present in the transfer vehicle.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but is not limited to, a polyethylene glycol chain of up to 5 kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

Preferably, the transfer vehicle (e.g., a lipid nanoparticle) is prepared by combining multiple lipid and/or polymer components. For example, a transfer vehicle may be prepared using DSPC/CHOL/DODAP/C8-PEG-5000 ceramide in a molar ratio of about 1 to 50:5 to 65:5 to 90:1 to 25, respectively. A transfer vehicle may be comprised of additional lipid combinations in various ratios, including for example, DSPC/CHOL/DODAP/mPEG-5000 (e.g., combined at a molar ratio of about 33:40:25:2), DSPC/CHOL/DODAP/C8 PEG-2000-Cer (e.g., combined at a molar ratio of about 31:40:25:4), POPC/DODAP/C8-PEG-2000-Cer (e.g., combined at a molar ratio of about 75-87:3-14:10) or DSPC/CHOL/DOTAP/C8 PEG-2000-Cer (e.g., combined at a molar ratio of about 31:40:25:4). The selection of cationic lipids, non-cationic lipids and/or PEG-modified lipids which comprise the liposomal transfer vehicle or lipid nanoparticle, as well as the relative molar ratio of such lipids to each other, is based upon the characteristics of the selected lipid(s), the nature of the intended target cells or tissues and the characteristics of the nucleic acids to be delivered by the liposomal transfer vehicle. Additional considerations include, for example, the saturation of the alkyl chain, as well as the size, charge, pH, pKa, fusogenicity and toxicity of the selected lipid(s).

The liposomal transfer vehicles for use in the present invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments of this invention, the compositions of the present invention comprise a transfer vehicle wherein the therapeutic RNA (e.g., mRNA encoding OTC) is associated on both the surface of the transfer vehicle (e.g., a liposome) and encapsulated within the same transfer vehicle. For example, during preparation of the compositions of the present invention, cationic liposomal transfer vehicles may associate with the nucleic acids (e.g., mRNA) through electrostatic interactions with such therapeutic mRNA.

In certain embodiments, the compositions of the present invention may be loaded with diagnostic radionuclide, fluorescent materials or other materials that are detectable in both in vitro and in vivo applications. For example, suitable diagnostic materials for use in the present invention may include Rhodamine-dioleoylphosphatidylethanolamine (Rh-PE), Green Fluorescent Protein mRNA (GFP mRNA), *Renilla* Luciferase mRNA and Firefly Luciferase mRNA.

During the preparation of liposomal transfer vehicles, water soluble carrier agents may be encapsulated in the aqueous interior by including them in the hydrating solution, and lipophilic molecules may be incorporated into the lipid bilayer by inclusion in the lipid formulation. In the case of certain molecules (e.g., cationic or anionic lipophilic nucleic acids), loading of the nucleic acid into preformed liposomes may be accomplished, for example, by the methods described in U.S. Pat. No. 4,946,683, the disclosure of which is incorporated herein by reference. Following encapsulation of the nucleic acid, the liposomes may be processed to remove un-encapsulated mRNA through processes such as gel chromatography, diafiltration or ultrafiltration. For example, if it is desirous to remove externally bound nucleic acid from the surface of the liposomal transfer vehicle formulation, such liposomes may be subject to a Diethylaminoethyl SEPHACEL column.

In addition to the encapsulated nucleic acid, one or more therapeutic or diagnostic agents may be included in the transfer vehicle. For example, such additional therapeutic agents may be associated with the surface of the liposome, can be incorporated into the lipid bilayer of a liposome by inclusion in the lipid formulation or loading into preformed liposomes (see U.S. Pat. Nos. 5,194,654 and 5,223,263, which are incorporated by reference herein). There are several methods for reducing the size, or "sizing", of liposomal transfer vehicles, and any of these methods may generally be employed when sizing is used as part of the invention. The extrusion method is a preferred method of liposome sizing. (Hope, M J et al. Reduction of Liposome Size and Preparation of Unilamellar Vesicles by Extrusion Techniques. In: Liposome Technology (G. Gregoriadis, Ed.) Vol. 1. p 123 (1993). The method consists of extruding liposomes through a small-pore polycarbonate membrane or an asymmetric ceramic membrane to reduce liposome sizes to a relatively well-defined size distribution. Typically, the suspension is cycled through the membrane one or more times until the desired liposome size distribution is achieved. The liposomes may be extruded through successively smaller pore membranes to achieve gradual reduction in liposome size.

A variety of alternative methods known in the art are available for sizing of a population of liposomal transfer vehicles. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421-450 (1981), incorporated herein by reference. Average liposome diameter may be reduced by sonication of formed liposomes. Intermittent sonication cycles may be alternated with QELS assessment to guide efficient liposome synthesis.

Selection of the appropriate size of a liposomal transfer vehicle must take into consideration the site of the target cell or tissue and to some extent the application for which the liposome is being made. In some embodiments, it may be desirable to limit transfection of the nucleic acids to certain cells or tissues. For example, the liver represents an important target organ for the compositions of the present invention in part due to its central role in metabolism and production of proteins and accordingly diseases which are caused by defects in liver-specific gene products (e.g., the urea cycle disorders) may benefit from specific targeting of cells (e.g., hepatocytes). Accordingly, in one embodiment of the present invention, the structural characteristics of the target tissue may be exploited to direct the distribution of the liposomal transfer vehicle to such target tissues. For example, to target hepatocytes a liposomal transfer vehicle may be sized such that its dimensions are smaller than the fenestrations of the endothelial layer lining hepatic sinusoids in the liver; accordingly the liposomal transfer vehicle can readily penetrate such endothelial fenestrations to reach the target hepatocytes. Alternatively, a liposomal transfer vehicle may be sized such that the dimensions of the liposome are of a sufficient diameter to limit or expressly avoid distribution into certain cells or tissues. For example, a liposomal transfer vehicle may be sized such that its dimensions are larger than the fenestrations of the endothelial layer lining hepatic sinusoids to thereby limit distribution of the liposomal transfer vehicle to hepatocytes. In such an embodiment, large liposomal transfer vehicles will not easily penetrate the endothelial fenestrations, and would instead be cleared by the macrophage Kupffer cells that line the liver sinusoids. Generally, the size of the transfer vehicle is within the range of about 25 to 250 nm, preferably less than about 250 nm, 175 nm, 150 nm, 125 nm, 100 nm, 75 nm, 50 nm, 25 nm or 10 nm.

Similarly, the compositions of the present invention may be prepared to preferentially distribute to other target tissues, cells or organs, such as the heart, lungs, kidneys, spleen. For example, the transfer vehicles of the present invention may be prepared to achieve enhanced delivery to the target cells and tissues. Accordingly, the compositions of the present invention may be enriched with additional cationic, non-cationic and PEG-modified lipids to further target tissues or cells.

In some embodiments, the compositions of the present invention distribute into the cells and tissues of the liver to facilitate the delivery and the subsequent expression of the nucleic acids (e.g., mRNA) comprised therein by the cells and tissues of the liver (e.g., hepatocytes). While such compositions may preferentially distribute into the cells and tissues of the liver, the therapeutic effects of the expressed nucleic acids need not be limited to the target cells and tissues. For example, the targeted hepatocytes may function as a "reservoir" or "depot" capable of expressing or producing, and systemically excreting a functional protein or enzyme. Accordingly, in one embodiment of the present invention the liposomal transfer vehicle may target hepatocyes and/or preferentially distribute to the cells and tissues of the liver and upon delivery. Following transfection of the target hepatocytes, the mRNA nucleic acids(s) loaded in the liposomal vehicle are translated and a functional protein product expressed, excreted and systemically distributed.

In some embodiments, the compositions of the present invention comprise one or more additional molecules (e.g., proteins, peptides, aptamers or oliogonucleotides) which facilitate the transfer of the nucleic acids (e.g., mRNA, miRNA, snRNA and snoRNA) from the transfer vehicle into an intracellular compartment of the target cell. In one embodiment, the additional molecule facilitates the delivery of the nucleic acids into, for example, the cytosol, the lysosome, the mitochondrion, the nucleus, the nucleolae or the proteasome of a target cell. Also included are agents that facilitate the transport of the translated protein of interest from the cytoplasm to its normal intercellular location (e.g., in the mitochondrion) to treat deficiencies in that organelle. In some embodiments, the agent is selected from the group consisting of a protein, a peptide, an aptamer, and an oligonucleotide.

In one embodiment, the compositions of the present invention facilitate a subject's endogenous production of one or more functional proteins and/or enzymes, and in particular the production of proteins and/or enzymes which demonstrate less immunogenicity relative to their recombinantly-prepared counterparts. In a preferred embodiment of the present invention, the transfer vehicles comprise nucleic acids which encode mRNA of a deficient protein or enzyme. Upon distribution of such compositions to the target tissues and the subsequent transfection of such target cells, the exogenous mRNA loaded into the liposomal transfer vehicle (e.g., a lipid nanoparticle) may be translated in vivo to produce a functional protein or enzyme encoded by the exogenously administered mRNA (e.g., a protein or enzyme in which the subject is deficient). Accordingly, the compositions of the present invention exploit a subject's ability to translate exogenously- or recombinantly-prepared mRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of mRNA encoding a deficient protein or enzyme avoids the need to deliver the nucleic acids to specific organelles within a target cell (e.g., mitochondria). Rather, upon transfection of a target cell and delivery of the nucleic acids to the cytoplasm of the target cell, the mRNA contents of a transfer vehicle may be translated and a functional protein or enzyme expressed.

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly may provide means to passively direct the delivery of the compositions to such target cells.

Alternatively, the present invention contemplates active targeting, which involves the use of additional excipients, referred to herein as "targeting ligands" that may be bound (either covalently or non-covalently) to the transfer vehicle to encourage localization of such transfer vehicle at certain target cells or target tissues. For example, targeting may be mediated by the inclusion of one or more endogenous targeting ligands (e.g., apolipoprotein E) in or on the transfer vehicle to encourage distribution to the target cells or tissues. Recognition of the targeting ligand by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a ligand capable of enhancing affinity of the composition to the target cell. Targeting ligands may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. No. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more ligands (e.g., peptides, aptamers, oligonucleotides, a vitamin or other molecules) that are capable of enhancing the affinity of the compositions and their nucleic acid contents for the target cells or tissues. Suitable ligands may optionally be bound or linked to the surface of the transfer vehicle. In some embodiments, the targeting ligand may span the surface of a transfer vehicle or be encapsulated within the transfer vehicle. Suitable ligands and are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the present invention may bear surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the transfer vehicle (e.g., a lipid nanoparticle) therefore facilitate recognition and uptake of the compositions of the present invention in target cells and tissues. Examples of suitable targeting ligands include one or more peptides, proteins, aptamers, vitamins and oligonucleotides.

As used herein, the term "subject" refers to any animal (e.g., a mammal), including, but not limited to, humans, non-human primates, rodents, and the like, to which the compositions and methods of the present invention are administered. Typically, the terms "subject" and "patient" are used interchangeably herein in reference to a human subject.

As used herein, the term "target cell" refers to a cell or tissue to which a composition of the invention is to be directed or targeted. In some embodiments, the target cells are deficient in a protein or enzyme of interest. For example, where it is desired to deliver a nucleic acid to a hepatocyte, the hepatocyte represents the target cell. In some embodiments, the nucleic acids and compositions of the present invention transfect the target cells on a discriminatory basis (i.e., do not transfect non-target cells). The compositions and methods of the present invention may be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by the compositions and nucleic acids of the present invention, expression of the protein encoded by such nucleic acid may be preferably stimulated and the capability of such target cells to express the protein of interest is enhanced. For example, transfection of a target cell with an mRNA OTC will allow expression of the protein product OTC following translation of the nucleic acid.

The urea cycle metabolic disorders and protein or enzyme deficiencies generally may be amenable to treatment with the methods and compositions provided herein. The nucleic acids of the compositions and/or methods provided herein preferably encode a product (e.g., a protein, enzyme, polypeptide, peptide, functional RNA, and/or antisense molecule), and preferably encodes a product whose in vivo production is desired.

The urea cycle metabolic disorders represent examples of protein and enzyme deficiencies which may be treated using the methods and compositions provided herein. Such urea cycle metabolic disorders include OTC deficiency, argino-succinate synthetase deficiency (ASD) and argininosuccinate lyase deficiency (ALD). Therefore, in some embodiments, the nucleic acid of the methods and compositions provided herein encode an enzyme involved in the urea cycle, including, for example, ornithine transcarbamylase (OTC), carbamyl phosphate synthetase (CPS), argininosuccinate synthetase 1 (ASS1) argininosuccinate lyase (ASL), and arginase (ARG).

Five metabolic disorders which result from defects in the biosynthesis of the enzymes involved in the urea cycle have been described, and include ornithine transcarbamylase (OTC) deficiency, carbamyl phosphate synthetase (CPS) deficiency, argininosuccinate synthetase 1 (ASS1) deficiency (citrullinemia), argininosuccinate lyase (ASL) deficiency and arginase deficiency (ARG). Of these five metabolic disorders, OTC deficiency represents the most common, occurring in an estimated one out of every 80,000 births.

OTC is a homotrimeric mitochondrial enzyme which is expressed almost exclusively in the liver and which encodes a precursor OTC protein that is cleaved in two steps upon incorporation into the mitchondrial matrix. (Horwich A L., et al. Cell 1986; 44: 451-459). OTC deficiency is a genetic disorder which results in a mutated and biologically inactive form of the enzyme ornithine transcarbamylase. OTC deficiency often becomes evident in the first few days of life, typically after protein ingestion. In the classic severe form of OTC deficiency, within the first days of life patients present with lethargy, convulsions, coma and severe hyperammonemia, which quickly leads to a deteriorating and fatal outcome absent appropriate medical intervention. (Monish S., et al., Genetics for Pediatricians; Remedica, Cold Spring Harbor Laboratory (2005)). If improperly treated or if left untreated, complications from OTC deficiency may include developmental delay and mental retardation. OTC deficient subjects may also present with progressive liver damage, skin lesions, and brittle hair. In some affected individuals, signs and symptoms of OTC deficiency may be less severe, and may not appear until later in life.

The OTC gene, which is located on the short arm of the X chromosome within band Xp21.1, spans more than 85 kb and is comprised of 10 exons encoding a protein of 1062 amino acids. (Lindgren V., et al. Science 1984; 226: 698-7700; Horwich, A L., et al. Science 224: 1068-1074, 1984; Horwich, A L. et al., Cell 44: 451-459, 1986; Hata, A., et al., J. Biochem. 100: 717-725, 1986, which are incorporated herein by reference). The OTC enzyme catalyzes the conversion or ornithine and carbamoyl phosphate to citrulline. Since OTC is on the X chromosome, females are primarily carriers while males with nonconservative mutations rarely survive past 72 hours of birth.

In healthy subjects, OTC is expressed almost exclusively in hepatocellular mitochondria. Although not expressed in the brain of healthy subjects, OTC deficiency can lead to neurological disorders. For example, one of the usual symptoms of OTC deficiency, which is heterogeneous in its presentation, is hyperammonaemic coma (Gordon, N., Eur J Paediatr Neurol 2003; 7:115-121.).

OTC deficiency is very heterogeneous, with over 200 unique mutations reported and large deletions that account for approximately 10-15% of all mutations, while the remainder generally comprises missense point mutations with smaller numbers of nonsense, splice-site and small deletion mutations. (Monish A., et al.) The phenotype of OTC deficiency is extremely heterogeneous, which can range from acute neonatal hyperammonemic coma to asymptomatic hemizygous adults. (Gordon N. Eur J Paediatr Neurol 2003; 7: 115-121). Those mutations that result in severe and life threatening neonatal disease are clustered in important structural and functional domains in the interior of the protein at sites of enzyme activity or at the interchain surface, while mutations associated with late-onset disease are located on the protein surface (Monish A., et al.) Patients with milder or partial forms of OTC deficiency may have onset of disease later in life, which may present as recurrent vomiting, neurobehavioral changes or seizures associated with hyperammonemia.

The compositions and methods of the present invention are broadly applicable to the delivery of nucleic acids, and in particular mRNA, to treat a number of disorders. In particular, the compositions and methods of the present invention are suitable for the treatment of diseases or disorders relating to the deficiency of proteins and/or enzymes. In one embodiment, the nucleic acids of the present invention encode functional proteins or enzymes that are excreted or secreted by the target cell into the surrounding extracellular fluid (e.g., mRNA encoding hormones and neurotransmitters). Alternatively, in another embodiment, the nucleic acids of the present invention encode functional proteins or enzymes that remain in the cytosol of the target cell (e.g., mRNA encoding urea cycle metabolic disorders). Other disorders for which the present invention are useful include disorders such as SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS IIIB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; and Wilson's disease. In one embodiment, the nucleic acids, and in particular mRNA, of the present invention may encode functional proteins or enzymes. For example, the compositions of the present invention may include mRNA encoding erythropoietin, α1-antitrypsin, carboxypeptidase N or human growth hormone.

Alternatively the nucleic acids may encode full length antibodies or smaller antibodies (e.g., both heavy and light chains) to confer immunity to a subject. While one embodiment of the present invention relates to methods and compositions useful for conferring immunity to a subject (e.g., via the translation of mRNA nucleic acids encoding functional antibodies), the inventions disclosed herein and contemplated hereby are broadly applicable. In an alternative embodiment the compositions of the present invention encode antibodies that may be used to transiently or chronically effect a functional response in subjects. For example, the mRNA nucleic acids of the present invention may encode a functional monoclonal or polyclonal antibody, which upon translation (and as applicable, systemic excretion from the target cells) may be useful for targeting and/or inactivating a biological target (e.g., a stimulatory cytokine such as tumor necrosis factor). Similarly, the mRNA nucleic acids of the present invention may encode, for example, functional anti-nephritic factor antibodies useful for the treatment of membranoproliferative glomerulonephritis type II or acute hemolytic uremic syndrome, or alternatively may encode anti-vascular endothelial growth factor (VEGF) antibodies useful for the treatment of VEGF-mediated diseases, such as cancer.

The compositions of the present invention can be administered to a subject. In some embodiments, the composition is formulated in combination with one or more additional nucleic acids, carriers, targeting ligands or stabilizing reagents, or in pharmacological compositions where it is mixed with suitable excipients. For example, in one embodiment, the compositions of the present invention may be prepared to deliver nucleic acids (e.g., mRNA) encoding two or more distinct proteins or enzymes. Alternatively, the compositions of the present invention may be prepared to deliver a single nucleic acid and two or more populations or such compositions may be combined in a single dosage form or co-administered to a subject. Techniques for formulation and administration of drugs may be found in "Remington's Pharmaceutical Sciences," Mack Publishing Co., Easton, Pa., latest edition.

A wide range of molecules that can exert pharmaceutical or therapeutic effects can be delivered into target cells using compositions and methods of the present invention. The molecules can be organic or inorganic. Organic molecules can be peptides, proteins, carbohydrates, lipids, sterols, nucleic acids (including peptide nucleic acids), or any combination thereof. A formulation for delivery into target cells can comprise more than one type of molecule, for example, two different nucleotide sequences, or a protein, an enzyme or a steroid.

The compositions of the present invention may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient expression of the nucleic acid in the target cell.

Suitable routes of administration include, for example, oral, rectal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, the compositions of the present invention may be administered in a local rather than systemic manner, for example, via injection of the pharmaceutical composition directly into a targeted tissue, preferably in a depot or sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present invention complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In one embodiment, the compositions of the present invention are formulated such that they are suitable for extended-release of the nucleic acids contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomal vehicles which are formulated for depot administration (e.g., intramuscularly, subcutaneously, intravitreally) to either deliver or release a nucleic acids (e.g., mRNA) over extended periods of time. Preferably, the extended-release means employed are combined with modifications made to the nucleic acid to enhance stability.

While certain compounds, compositions and methods of the present invention have been described with specificity in accordance with certain embodiments, the following examples serve only to illustrate the compounds of the invention and are not intended to limit the same. Each of the publications, reference materials, accession numbers and the like referenced herein to describe the background of the invention and to provide additional detail regarding its practice are hereby incorporated by reference in their entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXEMPLIFICATION

Example 1—General Preparation of Transfer Vehicles by Solvent Dilution Technique This example generally illustrates a process for the manufacture of small (<100 nm) liposomal formulations containing mRNA and the means to evaluate the amount of mRNA encapsulated. Parameters which may be modified to further optimize transfection efficiency include, but are not limited to, the selection of lipid, the ratio of lipids, the molar ratio of the PEG-containing lipid, the length of the lipid anchor of the PEG-containing lipid and the sizing of the liposomal transfer vehicles.

Appropriate quantities of lipids (e.g., DSPC/CHOL/DODAP/C8-PEG2000-Cer) to construct a transfer vehicle of a desired lipid ratio (e.g., a molar ratio of 31:40:25:4) were weighed and dissolved in absolute ethanol at 70° C. to obtain the desired lipid ratios and concentrations. In order to monitor the lipid, a small amount (typically 0.05 mole %) of rhodamine-dioleoylphosphatidylethanolamine (Rh-PE) was routinely added to the lipid solution.

mRNA, for example, encoding for GFP, OTC or Luciferase was denatured by heating for 10 minutes at 70° C., followed by cooling on ice. This solution was analyzed to confirm the mRNA concentration prior to formulation. An aliquot of mRNA was diluted with water, and then combined with an equal volume of 10 mM citrate pH 5.0 buffer such that the final citrate content following lipid addition (from solvent) was 4 mM.

The mRNA/citrate buffer solutions were then heated to 90° C. for 5 minutes to completely denature the mRNA. While stirring or vortexing the denatured mRNA, the ethanolic lipid solution (at 70° C.) was added to the mRNA to generate multi-lamellar vesicles (MLVs). The MLVs were then cooled to 70° C. prior to extrusion. For samples prepared at high solvent concentrations (>20%), the MLVs were diluted with 5 mM pH 5.0 citrate buffer (at 70° C.) to produce a solvent concentration of 20% before extrusion to generate large unilamellar vesicles (LUVs).

MLVs were extruded at 70° C. through 3 stacked 80 nm polycarbonate filters, using a thermo-jacketed extruder. Five passes were routinely used to generate large unilamellar vesicles (LUVs) of the desired size range. Following extrusion, the formulations were filtered through a 0.2 µm syringe filter to remove small amounts of particulate material that tended to interfere with the determination of vesicle size.

mRNA that was not associated with the liposomes or was associated with the exterior surface of DODAP-containing liposomes was removed by anion exchange, such that all remaining associated mRNA was encapsulated in the liposomes. Two suitable methods include the use of anion exchange using Acrodisc units with MUSTANG Q membranes (Pall Life Sciences), or anion exchange using DEAE-SEPHACEL (Sigma-Aldrich, suspension in 20% ethanol). These techniques allowed for efficient removal of unencapsulated mRNA without significant dilution of the formulations.

Following removal of external mRNA, buffer could be exchanged by use of PD-10 gel filtration columns (SEPHADEX G-25, GE Healthcare) using a spin protocol, which permits small molecular weight constituents (such as solvent and borate) in the liposome formulation to be retained in the gel and replaced by the equilibration buffer, without significant dilution of the sample. Alternatively, in some experiments, solvent may be removed and buffer exchanged using a Spectrum 500,000 MWCO diafiltration cartridge. Samples were ultrafiltered to 2-10 mL, then diafiltered against 10 wash volumes of the desired final buffer to remove solvent and exchange the buffer. The sample was sometimes further concentrated by ultrafiltration after the diafiltration process.

To quantify mRNA in samples with low lipid:mRNA ratios, a standard curve of mRNA was prepared by diluting the stock solution with water to obtain standards in the range of 0-200 µg/mL. Samples were diluted (based on expected mRNA concentrations) with the appropriate buffer to produce mRNA concentrations within the standard range. 180 µL aliquots of the standards or samples were combined with 300 µL of 5% SDS and 120 µL of ethanol. The samples were incubated for 10 min. at 50° C. to dissolve the lipid. After cooling, the samples were transferred in duplicate (250 µL aliquots) into the wells of a UV-transparent microplate. The absorbance at 260 nm was measured and the mRNA concentration in the samples calculated from the standard curve. In samples where the lipid:mRNA (weight:weight) ratio was 10:1 (target ratio) or less, interference from the lipids with the absorbance at 260 nm was relatively low and could be ignored.

In samples where the lipid:mRNA (weight:weight) ratio was greater than 10:1, lipid interference became more significant as the amount of lipid increased, and therefore the lipid had to be removed in order to accurately quantify the mRNA content. A standard curve of mRNA was prepared by diluting the stock solution with water to obtain standards in the range of 0-250 µg/mL. The samples to be assessed were diluted (based on expected mRNA concentrations) with the appropriate buffer to produce mRNA concentrations within the standard range. 180 µL of the standards or samples were combined with 20 µL 0.1 M sodium borate (to increase the pH, thus neutralizing the charge on the DODAP in the liposome samples, and causing the mRNA to dissociate from the DODAP). 600 µL of chloroform:methanol (1:2, v:v) was added to each standard or sample and the samples were vortexed. 200 µL of chloroform was added with vortexing followed by the addition of 200 µL of water. The samples were vigorously vortexed and then centrifuged for 2 min. at 1000×g to separate the phases. 250 µL aliquots of the upper (aqueous) phase were transferred (in duplicate) into the wells of a UV-transparent microplate and the absorbance at 260 nm was measured. The mRNA concentration in samples was calculated from the standard curve. Note that for liposome samples containing DOTAP (or any other cationic lipid that cannot be neutralized by incubation at high pH), this assay is unsuitable for determining mRNA concentration as the mRNA cannot be disassociated from the DOTAP and a proportion of the mRNA tends to be extracted into the solvent ($CHCl_3$) phase in conjunction with the lipid.

mRNA encapsulation was determined by separation of samples on DEAE-SEPHACEL (anion exchange gel) columns as follows. Using 2 mL glass Pasteur pipettes plugged with glass wool, columns of DEAE-SEPHACEL were poured and equilibrated with 5 volumes (~10 mL) of 145 mM sodium chloride-10 mM borate buffer pH 8.0. 0.5 mL of sample was loaded onto a column and the eluate collected. The columns were washed with 7×0.5 mL aliquots of 145 mM sodium chloride-10 mM borate buffer pH 8.0, collecting each eluted fraction separately. The initial sample and each aliquot was assayed for mRNA and lipid as described above. The % encapsulation was calculated by 100×(mRNA/lipid) of material eluted from the column/(mRNA/lipid) of initial sample). Based on the calculated mRNA concentration from extraction analyses described above liposomal mRNA samples were diluted to a desired mRNA concentration (1 µg) in a total volume of 5 µL (i.e. 0.2 mg/mL).

Example 2—Preparation of DSPC/CHOL/DODAP/C8-PEG-2000 Ceramide (Molar Ratio of 31:40:25:4)/Renilla Luciferase mRNA (Formulation 1)

Formulation 1 was prepared by dissolving the appropriate masses of DSPC, CHOL, DODAP and C8-PEG-2000 ceramide in absolute ethanol, then adding this to a solution of Renilla Luciferase mRNA in buffer to produce MLVs at 10.8 mg/mL lipid, 250 µg/mL mRNA, 20% solvent. The MLVs were extruded to produce LUVs, and then passed through a 0.2 µm filter. The pH was increased by combining with an equal volume of 100 mM NaCl-50 mM borate pH 8.0 and the external mRNA removed by anion exchange using the DEAE-Sephacel centrifugation method, as described in Example 1. The solvent was removed, the external buffer exchanged and the sample concentrated by diafiltration/ultrafiltration. The concentrated sample was then passed through a 0.2 µm filter and aliquots were transferred to vials and stored at 2-8° C.

Example 3—Preparation of DSPC/CHOL/DOTAP/C8-PEG-2000 Ceramide (Molar Ratio of 31:40:25:4)/*Renilla* Luciferase mRNA (Formulation 2)

Formulation 2 was prepared using a similar methodology as Formulation 1 with minor changes. In brief, the appropriate masses of DSPC, CHOL, DOTAP and C8-PEG-2000 ceramide were dissolved in absolute ethanol and then added to a solution of *Renilla* Luciferase mRNA in buffer to produce MLVs at 10.8 mg/mL lipid, 250 µg/mL mRNA, 20% solvent. The MLVs were extruded to produce LUVs. As DOTAP was used in this formulation, the external mRNA could not be effectively removed by anion exchange and therefore this step was omitted. The solvent was removed, the external buffer exchanged and the sample concentrated by diafiltration/ultrafiltration. The concentrated sample was then passed through a 0.2 µm filter and aliquots were transferred to vials and stored at 2-8° C.

Example 4—Preparation of DSPC/CHOL/DODAP/C8-PEG-2000 Ceramide (Molar Ratio of 31:40:25:4)/Firefly Luciferase mRNA (Formulation 3)

To prepare Formulation 3 the appropriate masses of DSPC, CHOL, DODAP and C8-PEG-2000 ceramide were dissolved in absolute ethanol, then added to a solution of Firefly Luciferase mRNA in buffer to produce MLVs at 10.8 mg/mL lipid, 250 µg/mL mRNA, 20% solvent. The MLVs were extruded to produce LUVs, and then passed through a 0.2 µm filter. The pH was increased by combining with 0.1 volumes of 0.1 M sodium borate and the external mRNA removed by anion exchange using the DEAF-Sephacel column method described in Example 1. The solvent was removed, the external buffer exchanged and the sample concentrated by diafiltration/ultrafiltration. The concentrated sample was then passed through a 0.2 µm filter and aliquots were transferred to vials and stored at 2-8° C.

Example 5—Preparation of DSPC/CHOL/DODAP/C8-PEG-2000 Ceramide (Molar Ratio of 31:40:2:4)/Murine OTC mRNA (Formulation 4)

Formulation 4 was prepared by dissolving the appropriate mass of DSPC, CHOL, DODAP and C8-PEG-2000 ceramide in absolute ethanol, then adding this to a solution of murine OTC mRNA in buffer to produce MLVs at 10.8 mg/mL lipid, 250 µg/mL mRNA, 20% solvent. The MLVs were extruded to produce LUVs, and then passed through a 0.2 µm filter. The pH was increased by combining with 0.1 volumes of 0.1 M sodium borate and the external mRNA removed by anion exchange using the DEAE-Sephacel column method as described in Example 1. The solvent was removed, the external buffer exchanged and the sample concentrated by diafiltration/ultrafiltration. The concentrated sample was then passed through a 0.2 µm filter and aliquots were transferred to vials and stored at 2-8° C.

Example 6—Preparation and Characterization of the Imidiazole Cholesterol Ester Lipid (3S,10R, 13R,17R)-10,13-dimethyl-17-((R)-6-methylheptan-2-yl)-2,3,4,7,8,9,10,11,12,13,14,15,16,17-tetradeca-hydro-1H-cyclopenta[a]phenanthren-3-yl 3-(1H-imidazol-4-yl)propanoate; Imidazole Cholesterol Ester (ICE)

FIG. 1 depicts the reaction scheme for the synthesis of ICE. A mixture of trityl-deamino-histidine (1), (1.97 g, 5.15 mmol), cholesterol (2), (1.97 g, 5.1 mmol), dicyclohexylcarbodiimide (DCC), (2.12 g, 5.2 mmol) and dimethylaminopyridine (DMAP), (0.13 g, 1.0 mmol) in anhydrous benzene (100 ml) was stirred at ambient temperature for two days. The resulting suspension was filtered through Celite and the filtrate was removed under reduced pressure. The resulting foam was dried under high vacuum overnight to provide crude ester (3) which was used on the following step without purification.

The crude ester (3) was dissolved in anhydrous dichloromethane (DCM), (200 ml) and trifluoroacetic acid (TFA), (50 ml) was added at room temperature. The resulting solution was stirred at ambient temperature for 4 hours. Aqueous saturated $NaHCO_3$ (250 ml) was added carefully, followed by solid $Na_2CO_3$ until slightly basic.

The phases were separated and the aqueous layer was extracted with DCM (200 ml). The organic phases were washed with brine (200 ml), dried ($Na_2SO_4$) and filtered. The resulting filtrate was evaporated and the residue was dried under high vacuum overnight. Flash chromatography purification (silica gel, 0-10% methanol in chloroform) afforded the desired pure product (4) (1.07 g, 37% yield for two steps) as a white solid (mp: 192-194° C.).

$^1$H NMR ($CDCk_3$): δ 0.66 (s, 3H), 0.84-1.64 (m, 33H), 1.76-2.05 (m, 5H), 2.29 (d, 2H), 2.63 (t, 2H), 2.90 (t, 2H), 4.61 (m, 1H), 5.36 (d, 1H), 6.80 (s, 1H), 7.53 (s, 1H). $^{13}$C NMR ($CDCl_3$): δ 11.9, 18.8, 19.4, 21.1, 21.6, 22.6, 22.9, 23.9, 24.4, 27.8, 28.1, 28.3, 31.9, 34.5, 35.9, 36.3, 36.7, 37.0, 38.2, 39.6, 39.8, 42.4, 50.1, 56.2, 56.8, 74.1, 122.8, 134.7, 139.6, 173.4. APCI(+)-MS (m/z): Calcd. 509, Found 509. Elem. Anal. (C,H,N): Calcd. 77.90, 10.30, 5.51; Found 77.65, 10.37, 5.55.

Example 7—Formulation Protocol

A codon-optimized firefly luciferase messenger RNA represented by SEQ ID NO: 1 (FFL mRNA) was synthesized by in vitro transcription from a plasmid DNA template encoding the gene, which was followed by the addition of a 5' cap structure (Cap1) and a 3' poly(A) tail of approximately 200 nucleotides in length as determined by gel electrophoresis. (See, e.g., Fechter, P. et al., J. Gen. Virology, 86, 1239-1249 (2005), the contents of which are incorporated herein by reference in its entirety.) The 5' and 3' untranslated regions present in the FFL mRNA product are underlined (SEQ ID NO: 1).

Nanoparticulate transfer vehicles were formed via standard ethanol injection methods. (See, e.g., Ponsa, M., et al., Int. J. Pharm. 95, 51-56 (1993), the contents of which are incorporated herein by reference.) Ethanolic stock solutions of the lipids were prepared ahead of time at a concentration of 50 mg/mL and stored at −20° C. FFL mRNA was stored in water at a final concentration of 1 mg/mL at −80° C. until the time of use.

All mRNA concentrations were determined via the Ribogreen assay (Invitrogen). Encapsulation of mRNA was calculated by performing the Ribogreen assay both with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

Aliquots of 50 mg/mL ethanolic solutions of an imidazole cholesterol ester lipid (ICE), DOPE and DMG-PEG-2000 were mixed and diluted with ethanol to a final volume of 3 mL. The molar ratio of the prepared ICE:DOPE:DMG-PEG-2000 transfer vehicle was 70:25:5. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticulate suspension was filtered, diafiltrated with 1×PBS (pH 7.4), concentrated and stored at 2-8° C. The final concentration was equal to 1.73 mg/mL CO-FF mRNA (encapsulated), the $Z_{ave}$ was equal to 68.0 nm (with a $Dv_{(50)}$ of 41.8 nm, and a $Dv_{(90)}$ of 78.0 nm) and the Zeta potential was equal to +25.7 mV.

Biodistribution Analysis

All studies were performed using female CD-1 mice of approximately 3-weeks age at the beginning of each experiment. Samples were introduced by a single bolus tail-vein injection of an equivalent total dose of 200 µg of encapsulated FFL mRNA. Four hours post-injection the mice were sacrificed and perfused with saline.

The liver and spleen of each mouse was harvested, apportioned into three parts, and stored in either, (i) 10% neutral buffered formalin, (ii) snap-frozen and stored at −80° C. for bioluminescence analysis (see below), or for in situ hybridization studies, or (iii) liver sections were isolated in isopentane (2-methylbutane) bath, maintained at −35° C., rinsed with 1×PBS, lightly patted with a kimwipe to remove any excess fluid, placed in the bath for approximately 5-7 minutes, after which the liver was removed, wrapped in foil and stored in a small sterile plastic bag at −80° C. until ready for assay.

The bioluminescence assay was conducted using a Promega Luciferase Assay System (Item #E1500 Promega). Tissue preparation was performed as follows: Portions of the desired tissue sample (snap-frozen) were thawed, washed with RODI water and placed in a ceramic bead homogenization tube. The tissue was treated with lysis buffer and homogenized. Upon subjection to five freeze/thaw cycles followed by centrifugation at 4° C., the supernatant was transferred to new microcentrifuge tubes. Repeat and store tissue extracts at −80° C.

The Luciferase Assay Reagent was prepared by adding 10 mL of Luciferase Assay Buffer to Luciferase Assay Substrate and mix via vortex. 20 µL of homogenate samples was loaded onto a 96-well plate followed by 20 µL of plate control to each sample. Separately, 120 µL of Luciferase Assay Reagent (prepared as described above) was loaded onto each well of a 96-well flat bottomed plate. Each plate was inserted into the appropriate chambers using a Molecular Device Flex Station instrument and measure the luminescence (measured in relative light units (RLU)).

In Situ Hybridization
Tissue Slide Preparation

Slide preparation and analysis was performed as follows: Each liver was frozen at −35° C. according to the procedure described above. The frozen livers were cut into 6 micrometer sections and mounted onto glass microscope slides. Prior to in situ hybridization, the sections were fixed in 4% formaldehyde in phosphate buffered saline (PBS), treated with trienthanolamine/acetic anhydride and washed and dehydrated through a series of ethanol solutions.

cRNA Probe Preparation

DNA templates were designed consisting of pBSKII+ vector containing EcoRI and XbaI restriction sites for generation of the antisense and sense strands, respectively. cRNA transcripts were synthesized from these DNA templates (antisense and sense strands, each 700 bp) with T3 and T7 RNA polymerase, respectively. Templates were validated by cold RNA probe synthesis prior to making riboprobes with $^{35}$S-UTP. Both antisense and sense radiolabeled riboprobes were synthesized in vitro according to the manufacturer's protocol (Ambion) and labeled with 35S-UTP (>1, 000 Ci/mmol).

Hybridization and Washing Procedures

Sections were hybridized overnight at 55° C. in deionized formamide, 0.3 M NaCl, 20 mM Tris-HCl (pH 7.4), 5 mM EDTA, 10 mM $Na_2HPO_4$, 10% dextran sulfate, 1×Denhardt's reagent, 50 µg/mL total yeast RNA and 50-80,000 cpm/µL 35S labeled cRNA probe. The tissues were subjected to stringent washing at 65° C. in 50% formamide, 2×SSC, 10 mM DTT and washed in PBS before treatment with 20 µg/ml RNAse A at 37° C. for 30 minutes. Following washes in 2×SSC and 0.1×SSC for 10 minutes at 37° C., the slides were dehydrated and exposed to Kodak BioMaxMR x-ray film for 90 minutes then submitted to emulsion autoradiography for 11 and 24 hours exposure times.

Imaging of Liver Sections

Photographic development was carried out in Kodak D-19. Sections were counterstained lightly with cresyl violet and analyzed using brightfield and darkfield microscopy. Sense (control) riboprobes established the level of background signal.

In Vivo Bioluminescence Results

Figure 2:
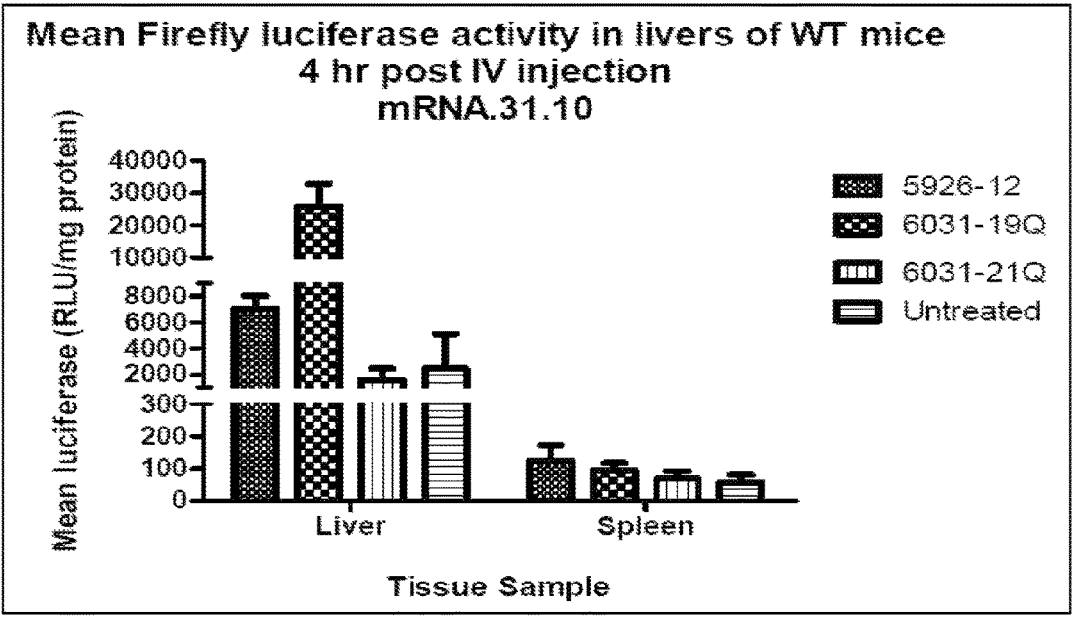
FIG. 2 illustrates the presence of firefly luciferase activity produced from the delivery of exogenous mRNA in the livers and spleens of treated and untreated CD-1 mice.

Animals were injected intravenously with a single 200 µg dose of encapsulated mRNA and sacrificed after four hours. Activity of expressed firefly luciferase protein in livers and spleens was determined in a bioluminescence assay. As demonstrated in FIG. 2, detectable signal over baseline was observed in every animal tested. The presence of a luminescent signal over background infers the expression of firefly luciferase protein from the exogenous mRNA. Luminescence observed in the liver was enhanced over similar signals observed in the spleen.

In Situ Hybridization Results

Figure 3:
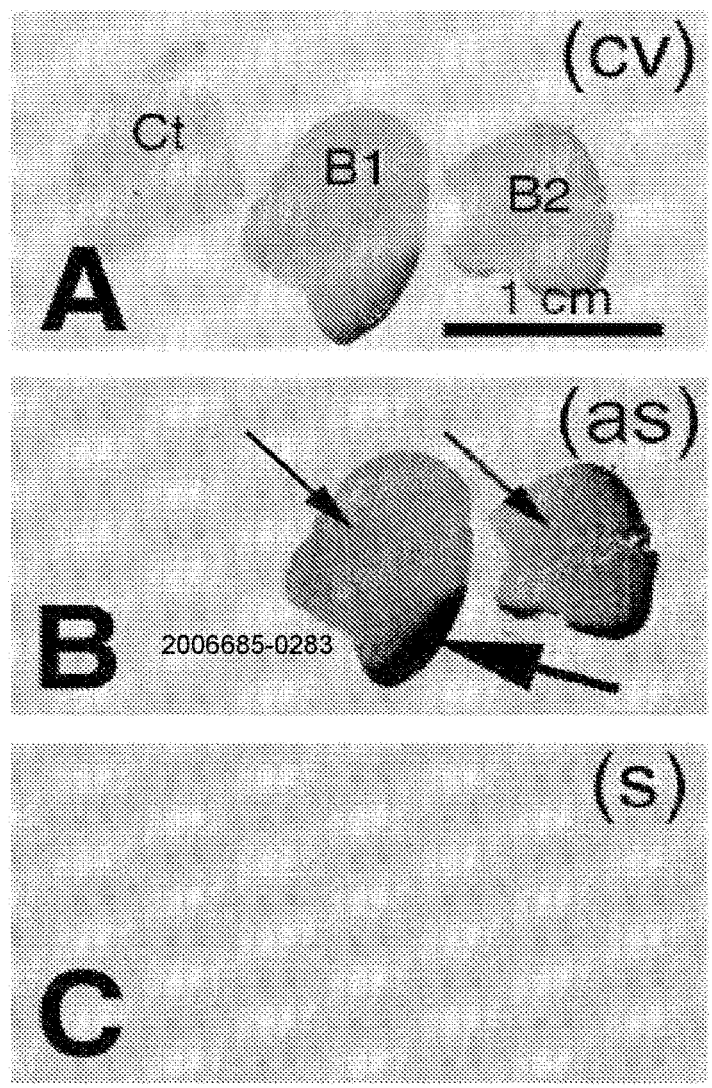
FIG. 3 illustrates codon-optimized firefly luciferase mRNA in situ hybridization in control and treated (B1 and B2) mouse livers observed on x-ray film under low (2x) magnification. (A) represents cresyl violet staining of control (Ct) and treated liver sections B1 and B2 mice; (B) represents X-ray film autoradiography detection by antisense probes of CO-FF luciferase mRNA in B1 and B2 mouse livers; and (C) represents control (sense) hybridization. The abbreviations "cv", "as" and "s" correspond to cresyl violet, antisense, and sense, respectively.

In situ hybridization studies were performed on liver taken from two different animals from the group of mice treated using an ICE:DOPE:DMG-PEG-2000 transfer vehicle (prepared as previously described) and one control liver from the untreated group of mice. X-Ray film autoradiography was employed for the detection of codon-optimized firefly luciferase mRNA via $^{35}$S-U labeled riboprobes. (See, Wilcox, J. N.J. Histochem. Cytochem. 41, 1725-1733 (1993)). FIG. 3 demonstrates both brightfield illumination (cresyl violet counterstain) and darkfield illumination of control and treated livers under low (2×) magnification. CO-FF luciferase mRNA was detected in both treated livers (B1 and B2, thin arrows) but not the control liver (Ct) when using the antisense riboprobe (FIG. 3B). High-level mRNA labeling was observed in the liver marginal tissue band (large arrow). No signal was detected in any liver when applying the control (sense) riboprobe (FIG. 3C).

Figure 4:
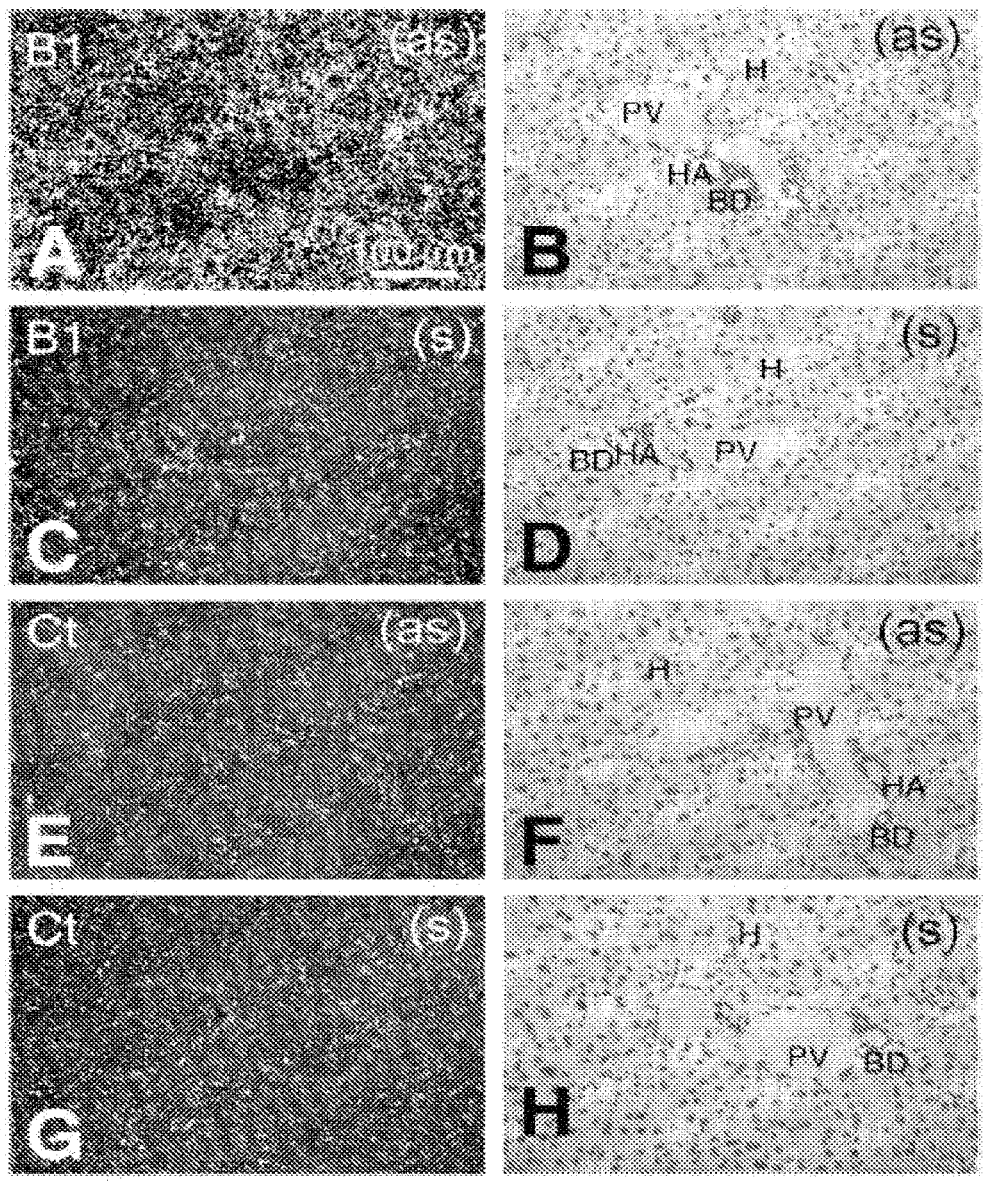
FIG. 4 illustrates codon-optimized firefly luciferase mRNA labeling in treated (B1) and control livers. (A) represents emulsion autoradiography detection of CO-FF luciferase mRNA in a B1 liver section seen as bright labeling under darkfield illumination; (B) represents the same region as (A) seen under brightfield illumination using cresyl violet as a counter-stain; (C) represents B1 liver section treated with the CO-FF luciferase control (sense) riboprobe establishing the level of non-specific labeling; (D) represents the same region as (C) seen under brightfield illumination; (E) represents untreated control liver section treated with CO-FF luciferase antisense probe, no signal was detected; (F) represents the same region as (E) seen under brightfield illumination; (G) represents control liver section treated with the CO-FF luciferase control (sense) riboprobe establishing the level of non-specific labeling; and (H) represents the same region as (G) seen under brightfield illumination. The abbreviations "BD", "HA", "H", "PV", "as" and "s" correspond to bile duct, hepatic artery, hepatocyte, portal vein, antisense and sense respectively. Magnification: 100x.

Under a dark field illumination labeled FFL mRNA was detected as bright spots (100× magnification) in the livers of injected animals by hybridization of an antisense probe of FFL mRNA (FIG. 4A), while the same liver showed few bright spots when a sense strand probe of FFL mRNA was used for hybridization (FIG. 4C). A control liver taken from an animal that did not receive any nanoparticles by injection did not produce any significant signal under dark field illumination when either the antisense (FIG. 4E) or sense probes (FIG. 4G) were used for hybridization.

Example 8—Immunohistochemical Analysis Results

The FFL mRNA was packaged and delivered via a lipid transfer vehicle formulation consisting of cholesterol, DOPE, DLinDMA, and DMG-PEG2000 in a manner similar to that described supra.

Figure 5:
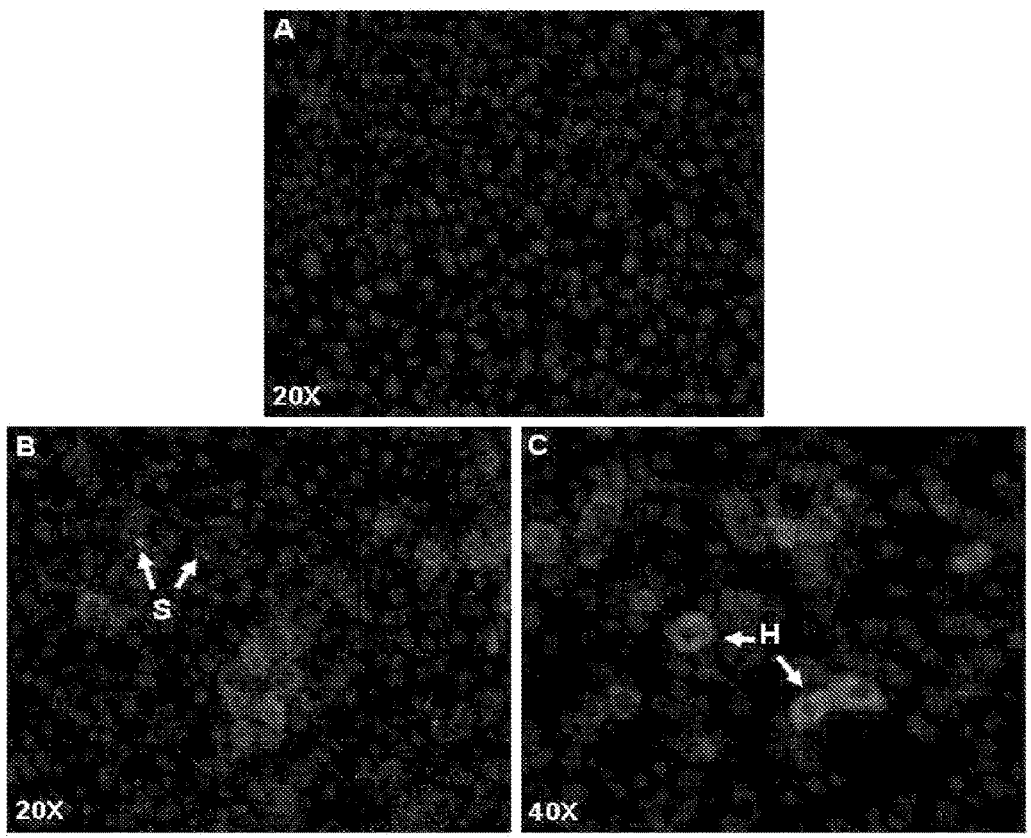
FIG. 5 illustrates immunohistochemical staining of mouse livers for the detection of firefly luciferase protein. (A) represents negative luciferase staining for control liver of mouse treated with 1×PBS (20×); (B) represents positive luciferase protein detection via immunohistochemical fluorescence-based methods, demonstrating that firefly luciferase protein is observed in the hepatocytes (20×), as well as a small number of sinusoidal endothelial cells that were positive for luciferase protein as well; (C) represents a positive firefly luciferase protein staining shown at higher magnification (40×). Luciferase protein is observed throughout the cytoplasm of the hepatocytes. The abbreviations (S) and (H) correspond to sinusoidal cells and hepatocytes, respectively.

The translation of the FFL mRNA into its respective protein has been successfully identified via immunohistochemical analysis (FIG. 5). Using an anti-firefly antibody, the detection of expressed firefly protein can be observed in the hepatocytes of treated mice (FIGS. 5B and 5C). The analysis of control mice treated with 1×PBS demonstrated no detectable firefly protein (FIG. 5A).

Discussion

A synthetic messenger RNA encapsulated in lipid-based materials can be used for the delivery and expression of genes in vivo in liver including heptocytes. Mixtures of cationic, non-cationic and PEG-modified lipids were used to express a reporter protein molecule. The imidazole-based cationic lipid ICE resulted in enriched delivery of mRNA to liver versus spleen in vivo. The observation of a bioluminescent signal demonstrates that a protein reporter molecule was translated from the exogenous mRNA that was delivered in a lipid nanoparticle in vivo. In situ hybridization studies demonstrated the direct detection of the exogenous mRNA through $^{35}$S-U riboprobe labeling. Emulsion autoradiography produced a signal that can be used to localize the mRNA to liver tissue and more specifically to hepatocytes present in the livers of treated animals (See, FIGS. 3 and 4). FFL mRNA was not detected in the livers of untreated control mice.

The successful delivery of such mRNA to the liver and in particular to hepatocytes supports the conclusion that the methods, formulations and compositions of the present invention can be used for the treatment and the correction of in-born errors of metabolism that are localized to the liver. For example, diseases such as ASD, ARG, CPS, ASS1 and OTC deficiencies, as well as other disorders may be treated through mRNA replacement therapy of a missing or malfunctioning gene. Metabolic zonation of the urea cycle to hepatocytes means that replacement of the missing enzyme activity in these cells should greatly improve normal biochemical processing in subjects afflicted by an enzyme deficiency, and in particular subjects afflicted with a urea cycle disorder.

What is claimed is:

1. A method of delivery of messenger RNA (mRNA) for in vivo production of protein, comprising
administering systemically to a subject in need of delivery a composition comprising an mRNA encoding a protein, encapsulated within a liposome such that the administering of the composition results in the prolonged stable expression of the protein encoded by the mRNA in the liver;
wherein the protein encoded by the mRNA is an enzyme, a hormone, a receptor or an antibody; and
wherein the liposome comprises one or more cationic lipids, one or more non-cationic lipids, one or more cholesterol-based lipids and one or more PEG-modified lipids and has a size less than about 100 nm.

2. The method of claim 1, wherein the one or more non-cationic lipids comprise DOPE.

3. The method of claim 1, wherein the one or more cationic lipids comprise DLinDMA, CLinDMA, or DLin-K-XTC2-DMA.

4. The method of claim 1, wherein the one or more PEG-modified lipids comprise DMG-PEG-2000 or C8-PEG-2000.

5. The method of claim 1, wherein the mRNA is of at least 30 kDa.

6. The method of claim 1, wherein the mRNA is modified to enhance stability.

7. The method of claim 6, wherein the mRNA is modified to include a modified nucleotide, an alteration to the 5' or 3' untranslated region, a cap structure or a poly A tail.

8. The method of claim 7, wherein the modified nucleotide is pseudouridine.

9. The method of claim 1, wherein the mRNA is unmodified.

10. The method of claim 1, wherein the protein encoded by the mRNA is a liver-specific enzyme.

11. The method of claim 10, wherein the enzyme is selected from ornithine transcarbamylase (OTC), carbamyl phosphate synthetase (CPS), argininosuccinate synthetase 1 (ASS1) argininosuccinate lyase (ASL), and arginase (ARG).

12. The method of claim 1, wherein the protein is retained within the cytosol of the liver cells after expression.

13. The method of claim 1, wherein the protein is secreted extracellularly after expression.

14. The method of claim 13, wherein the protein is systemically distributed.

15. The method of claim 1, wherein the composition is administered intravenously.

16. The method of claim 1, wherein the expression of the protein encoded by the mRNA in the liver is detectable at least 4 hours post administration.

17. The method of claim 1, wherein the composition comprises two or more mRNAs encoding two or more distinct proteins.

18. A method of treating a metabolic disorder comprising administering to a subject suffering from or susceptible to a metabolic disorder resulting from an enzyme deficiency, a composition comprising an mRNA encoding the enzyme, encapsulated within a liposome such that the administering of the composition results in increased expression of the enzyme encoded by the mRNA in the liver sufficient to treat the enzyme deficiency;
wherein the liposome comprises one or more cationic lipids, one or more or non-cationic lipids, one or more cholesterol-based lipids and one or more PEG-modified lipids and has a size less than about 100 nm.

19. The method of claim 18, wherein the metabolic disorder is a urea cycle disorder.

20. The method of claim 19, wherein the urea cycle disorder results from ornithine transcarbamylase (OTC) deficiency, carbamyl phosphate synthetase (CPS) deficiency, argininosuccinate synthetase 1 (ASS1) deficiency (citrullinemia), argininosuccinate lyase (ASL) deficiency or arginase deficiency (ARG).

21. The method of claim 18, wherein the enzyme is a liver specific enzyme.

22. The method of claim 18, wherein the composition is administered intravenously.

23. The method of claim 1, wherein the one or more cationic lipids carry a net positive charge at physiological pH.

24. The method of claim 23, wherein the one or more cationic lipids constitute about 20-70% mol % of the total lipids present in the liposome.

25. The method of claim 1, wherein the one or more PEG-modified lipids comprise a polyethylene glycol chain of up to 5 kDa in length covalently attached to a lipid with alkyl chain(s) of $C_6$-$C_{20}$ length.

26. The method of claim 1, wherein the one or more PEG-modified lipids constitute up to about 20 mol % of the total lipids present in the liposome.

27. The method of claim 1, wherein the composition is administered bi-weekly.

28. The method of claim 1, wherein the composition is administered monthly.

29. The method of claim 1, wherein the mRNA is administered systemically.

30. The method of claim 18, wherein the enzyme is selected from ornithine transcarbamylase (OTC), carbamyl phosphate synthetase (CPS), argininosuccinate synthetase 1 (ASS1) argininosuccinate lyase (ASL), and arginase (ARG).

* * * * *

SEQUENCE LISTING

```
<160> NUMBER OF SEQ ID NOS: 3

<210> SEQ ID NO 1
<211> LENGTH: 1672
<212> TYPE: RNA
<213> ORGANISM: Artificial
<220> FEATURE:
<223> OTHER INFORMATION: CO-FF Luciferase mRNA

<400> SEQUENCE: 1
gggauccuac cauggaagau gccaaaaaca uuaagaaggg cccagcgcca uucuacccac      60
ucgaagacgg gaccgccggc gagcagcugc acaaagccau gaagcgcuac gcccuggugc     120
ccggcaccau cgccuuuacc gacgcacaua ucgaggugga cauuaccuac gccgaguacu     180
ucgagaugag cguucggcug gcagaagcua ugaagcgcua ugggcugaau acaaaccauc     240
ggaucguggu gugcagcgag aauagcuugc aguucuucau gcccguguug ggugcccugu     300
ucaucggugu ggcuguggcc ccagcuaacg acaucuacaa cgagcgcgag cugcugaaca     360
gcaugggcau cagccagccc accgucguau ucgugagcaa gaaagggcug caaaagaucc     420
ucaacgugca aaagaagcua ccgaucauac aaaagaucau caucauggau agcaagaccg     480
acuaccaggg cuuccaaagc auguacaccu ucgugacuuc ccauuugcca cccggcuuca     540
acgaguacga cuucgugccc gagagcuucg accgggacaa aaccaucgcc cugaucauga     600
acaguagugg caguaccgga uugcccaagg gcguagcccu accgcaccgc accgcuugug     660
uccgauucag ucaugcccgc gaccccaucu ucggcaacca gaucauccc gacaccgcua     720 uccucagcgu gguccauuu caccacgcu ucggcauguu caccacgcug ggcuacuuga     780
ucugcggcuu ucgggucgug cucauguacc gcuucgagga ggagcuauuc uugcgcagcu     840
ugcaagacua uaagauucaa ucugcccugc uggugcccac acuauuuagc uucuucgcua     900
agagcacucu caucgacaag uacgaccuaa gcaacuugca cgagaucgcc agcggcgggg     960
```

```
cgccgcucag caaggaggua ggugaggccg uggccaaacg cuuccaccua ccaggcaucc    1020
gccagggcua cggccugaca gaaacaacca gcgccauucu gaucacccccc gaagggacg    1080 acaagccugg cgcaguaggc aaggugguggc ccuucuucga ggcuaaggug guggacuugg   1140
acaccgguaa gacacugggu gugaaccagc gcggcgagcu gucgcuccgu ggccccauga    1200
ucaugagcgg cuacguuaac aaccccgagg cuacaaacgc ucucaucgac aaggacggcu    1260
ggcugcacag cggcgacauc gccuacuggg acgaggacga gcacuucuuc aucguggacc    1320
ggcugaagag ccugaucaaa uacaagggcu accagguagc cccagccgaa cuggagagca    1380
uccugcugca acaccccaac aucuucgacg ccggggucgc cggccugccc gacgacgaug    1440
ccggcgagcu gcccgccgca gucgucgugc uggaacacgg uaaaaccaug accgagaagg    1500
agaucgugga cuauguggcc agccagguua caaccgccaa gaagcugcgc gguggugung   1560
uguucgugga cgaggugccu aaaggacuga ccggcaaguu ggacgcccgc aagauccgcg    1620
agauucucau uaaggccaag aagggcggca agaucgccgu guaauuugaa uu            1672

<210> SEQ ID NO 2
<211> LENGTH: 157
<212> TYPE: RNA
<213> ORGANISM: Artificial
<220> FEATURE:
<223> OTHER INFORMATION: 5' CMV Sequence

<400> SEQUENCE: 2
uaauacgacu cacuauagga cagaucgccu ggagacgcca uccacgcugu uuugaccucc      60
auagaagaca ccgggaccga uccagccucc gcggccggga acggugcauu ggaacgcgga    120
uuccccgugc caagagugac ucaccguccu ugacacg                             157

<210> SEQ ID NO 3
<211> LENGTH: 100
<212> TYPE: RNA
<213> ORGANISM: Artificial
<220> FEATURE:
<223> OTHER INFORMATION: 3' hGH Sequence

<400> SEQUENCE: 3
cggguggcau cccugugacc ccuccccagu gccucuccug gccuggaag uugccacucc       60 agugcccacc agccuugucc uaauaaaauu aaguugcauc                          100
```